(12) United States Patent
Palumbo

(10) Patent No.: US 10,078,051 B2
(45) Date of Patent: Sep. 18, 2018

(54) COMPENSATING TURBIDITY MEASURING DEVICE

(71) Applicant: TINTOMETER GMBH, Dortmund (DE)

(72) Inventor: Perry Palumbo, Fort Collins, CO (US)

(*) Notice: Subject to any disclaimer, the term of this patent is extended or adjusted under 35 U.S.C. 154(b) by 0 days.

(21) Appl. No.: 15/551,127

(22) PCT Filed: Mar. 30, 2017

(86) PCT No.: PCT/US2017/024900
§ 371 (c)(1),
(2) Date: Aug. 15, 2017

(87) PCT Pub. No.: WO2017/173020
PCT Pub. Date: Oct. 5, 2017

(65) Prior Publication Data
US 2018/0136123 A1    May 17, 2018

Related U.S. Application Data

(60) Provisional application No. 62/315,298, filed on Mar. 30, 2016.

(51) Int. Cl.
| | |
|---|---|
| G01N 21/00 | (2006.01) |
| G01N 21/53 | (2006.01) |
| G01N 15/06 | (2006.01) |
| G01J 1/18 | (2006.01) |
| G01N 11/08 | (2006.01) |
| G01N 21/01 | (2006.01) |

(52) U.S. Cl.
CPC ............. *G01N 21/532* (2013.01); *G01J 1/18* (2013.01); *G01N 11/08* (2013.01); *G01N 15/06* (2013.01); *G01N 21/01* (2013.01)

(58) Field of Classification Search
CPC ...... G01N 21/532; G01N 11/08; G01N 15/06; G01N 21/01; G01J 1/18
USPC .................................................. 356/335–343
See application file for complete search history.

(56) References Cited

U.S. PATENT DOCUMENTS

| | | |
|---|---|---|
| 4,129,140 A | 12/1978 | Carlin |
| 5,536,413 A | 7/1996 | Bormann et al. |
| 7,249,517 B2 | 7/2007 | Heuer et al. |
| 9,226,695 B2 | 1/2016 | Margalit |

FOREIGN PATENT DOCUMENTS

| | | |
|---|---|---|
| CN | 101403865 | 4/2009 |
| WO | 2015/105916 | 7/2015 |

*Primary Examiner* — Tri T Ton
(74) *Attorney, Agent, or Firm* — Leyendecker & Lemire, LLC

(57) ABSTRACT

Embodiments of the present invention can be implemented to (i) verify that a liquid within a turbidity measuring device during an assay process is of the same origin of that upon which the assay was performed, (ii) verify a flow through the turbidity measuring device including, but not limited to, a turbidimeter, a nephelometer, a fluorimeter, or the like, and (iii) enact an alteration to measurement step(s) and/or determination step(s) of an assay process in correlation with one or more variables associated with the liquid sample including, but not limited to, flow rate, temperature, and pressure to reduce a standard error of the assay.

18 Claims, 16 Drawing Sheets

COMPENSATING TURBIDITY MEASURING DEVICE

CROSS-REFERENCE TO RELATED APPLICATION

This application claims the benefit of U.S. Provisional Application No. 62/315,298, filed Mar. 30, 2016.

BACKGROUND

The assay of turbidity is an effective means for evaluating the level of contaminates and pathogens within a liquid stream. The determination of a constituent in a liquid flowing in a stream may be carried out using a variety of methods and techniques. A significant number of methods and analysis techniques currently rely on interrogating a liquid sample using optical means. The interrogation includes a beam of light, or other electromagnetic radiation, being transmitted through the liquid. The light will be absorbed, scattered, or stimulate fluorescence in proportion to a determinable component of the liquid, analyte, or contaminate of interest.

Entrained air and other gases present within the liquid sample can cause a portion of the beam of light to scatter as the light travels through the liquid sample resulting in a reduction in the transmission of light through the liquid and an increase of the observability of the beam within the liquid. The decrease in the transmission of light through the sample due to entrained air mimics absorption and is indistinguishable from that which is due to the analyte, contaminate, or pathogen. The observability of the beam due to entrained air likewise interferes with nephelometric or fluorometric determination methods as more light is scattered than can be accounted for due to particle content or fluorescence of the liquid sample.

It is therefore important for an accurate determination of the constituent of interest that air or other entrained gases be removed prior to interrogation of the liquid sample by a beam of light to the extent that the remaining air or gases have no significant contribution to the limit of detection of the method of analysis or is reduced to less than that which does not interfere with the determinable property of the liquid.

When the removal of entrained gases is incomplete due to changes in the measurement conditions (e.g., pressure, temperature, or flow rate of the liquid sample stream) other or additional means must be employed for removal of the interference from affecting an integrity of the value of interest. Other or additional means for removal of the fine bubble interference value from the turbidity value may be employed during the interrogation or determination steps. To this end, bubble rejection algorithms are commonly employed to diminish the error introduced by entrained gas within the assay process by eliminating statistical outliers from a measurement data series. At lower flow rates, the interference value due to fine gas bubbles is readily distinguishable from the turbidity value as the summary product of the interference value and the turbidity value. For instance, a baseline signal value is substantially equal to the turbidity value.

A signal value where the interference value is significantly higher than the baseline value may be readily removed from a given measurement set during the determination step as a statistical outlier. To disadvantage, at low flow rates the observability of fluctuations in the analyte concentration within an assay chamber is diminished due to a low exchange rate of the incoming liquid sample mixing with the existing liquid sample within a volume of the assay chamber.

Another consequence of too low a flow rate is an increase in the delay from when a change in concentration event occurs to when the change in concentration is observed. Of further consequence of flow rate on the assay determinability, as the liquid sample flow rate is increased, a greater number of fine gas bubbles are more often carried into the assay chamber of the analytical device making the baseline determination less obvious.

As the flow rate increases further, the frequency at which the interference value is superimposed upon the turbidity value continues to increase until a limit is reached where the baseline value becomes irreconcilable from the interference value. It is therefore necessary to reduce the flow rate or alter the measurement step(s) and/or determination step(s) so as the resulting baseline value is no longer obscured by the fine bubble interference. For instance, a flow rate where the interference rate does not exceed the Nyquist limit of the interrogation or measurement rate. Stated alternatively, in practice it is required that the liquid assay device, (e.g., the turbidimeter, nephelometer, or alike), be operated at a flow rate where the frequency at which interference value due to fine bubbles imprinted on the assay value does not exceed one half the assay measurement rate.

A further problem exists in the determination of flow rate at flows of less than 100 mL per minute, where the head pressure to the flow meter is low and the liquid sample is sedimentary in nature. Conventional flow meters such as paddle-wheel (turbine), differential pressure, variable area, caloric, positive displacement, Coriolis, weir height (open channel), and vortex type flow meters have a disadvantage of high cost, high power consumption, and/or are unreliable in conditions of low flow rates. They further require high head pressure and clog easily when used for measuring liquid samples containing particulate matter.

DETAILED DESCRIPTION

Figure 1:
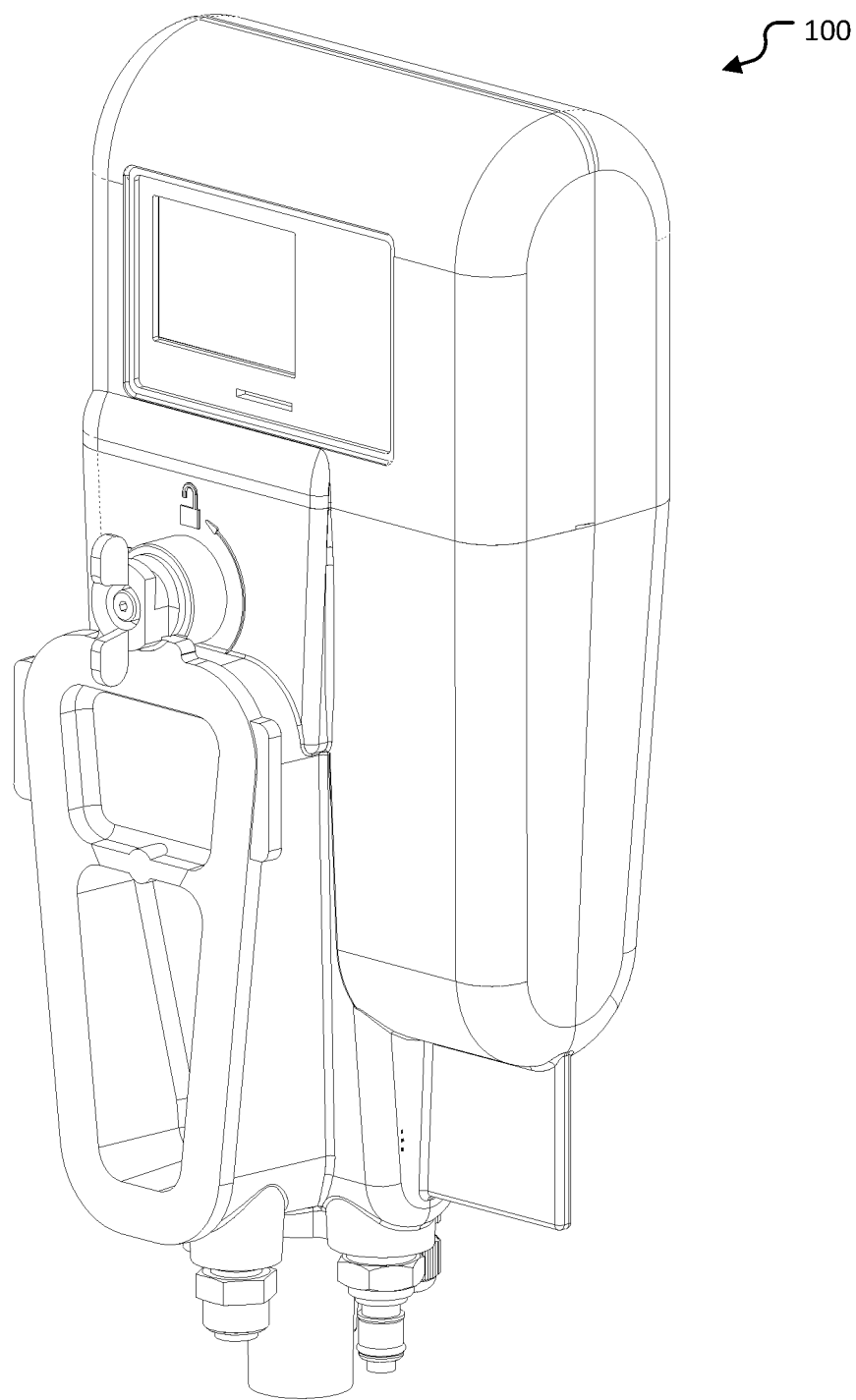
FIG. 1 is an isometric view of a turbidity measuring device according to one embodiment of the present invention.

Embodiments of the present invention include a turbidity measuring device including one or more means for measuring temperature, pressure, and flow rate of a liquid being assayed. In one embodiment, the turbidity measuring device can include, but is not limited to, a fluidic module, a measurement module, a means for measuring temperature, a means for measuring pressure, and a means for measuring a flow rate.

Embodiments can be implemented to (i) verify that a liquid within an turbidity measuring device during an assay process can be of the same origin of that upon which the assay was performed, (ii) verify a flow through the turbidity measuring device (e.g., a turbidimeter, a nephelometer, a fluorimeter, or the like), and (iii) enact an alteration to the measurement step(s) and/or determination step(s) of an assay process in correlation with one or more variables associated with the liquid sample including, but not limited to, flow rate, temperature, and/or pressure to reduce a standard error of the assay.

A first embodiment of the turbidity measuring device can include a turbidimeter having a fluidic module and a measurement module. The turbidimeter can include, but is not limited to, an inlet port, a first chamber, a second chamber, a third chamber, an illumination means, a means for detecting light, a means for measuring temperature, a determination means, a communication means, and an outlet port. The inlet port can be adapted for ingress of liquid into the turbidimeter. The first chamber can contain a liquid in communication with the inlet port and can be vented to atmosphere. The second chamber can be in communication with the first chamber containing liquid wherein a determination of one or more properties of a liquid can be made. The third chamber can contain a liquid where liquid from the second chamber can spill into the third chamber, excommunicating liquid from the second chamber. The illumination means can include a light source to form a light beam and subsequently propagate the light beam through liquid in the second chamber. The means of detecting light can detect light scattered by a liquid in proportion to content of a scattering agent within the liquid. The means for measuring temperature can be implemented to determine a temperature of the liquid within the second chamber. The determination means can be implemented to determine a value of turbidity according to an amount of light received by the detecting means and the temperature of the liquid within the second chamber. The communication means can electronically communicate the value of turbidity and/or can be configured to display the value of turbidity. The outlet port can be implemented for the egress of the liquid from the third chamber.

Another embodiment of the present invention includes the previously described turbidimeter that further includes a means for measuring pressure. The means for measuring pressure can be implemented to determine a pressure above the liquid in the second chamber. For instance, a pressure sensor can be implemented to determine an atmospheric pressure above the liquid in the second chamber. Typically, the determination means can determine a value of turbidity based on the amount of light received by the detecting means and the pressure above the liquid of the second chamber.

Yet another embodiment of the present invention includes the previously mentioned turbidimeter that further includes a means for determining flow rate. The means for determining flow rate can be implemented to determine a flow rate of the excommunicating liquid from the second chamber to the third chamber. Typically, the determination means can determine a value of turbidity based on the amount of light received by the detecting means and the flow rate of the excommunicating liquid from the second chamber.

A second embodiment of the turbidity measuring device can include a turbidimeter having a fluidic module and a measurement module. The second embodiment turbidimeter can include, but is not limited to, an inlet port, a first chamber, a second chamber, a third chamber, a tube within the third chamber, a means for determining if liquid is present, a determination means, an illumination means, a means for detecting light, and a communication means. The inlet port can be adapted for ingress of liquid into the turbidimeter. The first chamber can contain a liquid in communication with the inlet port and be vented to atmosphere. The second chamber can be in communication with the first chamber containing liquid wherein a determination of one or more properties of the liquid can be made. The third chamber can contain a liquid wherein liquid from the second chamber spills into the third chamber, excommunicating liquid from the second chamber.

In one embodiment, the tube can be a "U" shaped tube and can be positioned within the third chamber in a form of an inverted "U" having a bend and a pair of legs substantially parallel to one another. A first leg of the tube can be extend through a bottom of, and offset below the bottom of, the third chamber. The bend of the tube can be located below the spillway excommunicating liquid of the second chamber. A second leg, typically of regular length, can be substantially perpendicular to, and offset above the bottom of, the third chamber. A volume of liquid can be periodically drawn from the third chamber as result of negative pressure created by a flow through the tube when liquid within the third chamber exceeds a height of the bend in the tube.

In one instance, the means of determining the presence and/or absence of liquid can determine the presence and/or absence of liquid within the third chamber. The determination means can determine a flow rate of excommunicating liquid of the second chamber based on an elapsed time from one occurrence of the presence and/or absence of liquid within the third chamber to a subsequent occurrence of the presence and/or absence of liquid within the third chamber of a known volume. The illumination means can include a light source to form a light beam and subsequently propagate the light beam through liquid in the second chamber. The means of detecting light can detect light scattered by a liquid in proportion to a content of a scattering agent within the liquid. The communication means can electronically communicate the value of turbidity and/or can be configured to display the value of turbidity.

Another embodiment of the present invention can include the previously described second embodiment turbidimeter that further includes a means for determining a level of liquid. In one instance, the means of determining the level of liquid can determine the level of liquid within the third chamber. The determination means can determine a flow rate of excommunicating liquid of the second chamber based on an elapsed time from one occurrence of the level of liquid within the third chamber to a subsequent occurrence of the same level of liquid within the third chamber of a known volume.

Embodiments of the present invention further include a method whereby a flow rate of an excommunicating liquid from a second chamber of a previously described turbidimeter can be determined. In one embodiment, the flow rate can be determined by a process whereby: (i) a third chamber where liquid from a second chamber spills, excommunicating liquid from the second chamber; (ii) liquid ingress to the third chamber causes a rise in a liquid level within the third chamber, submersing a high end of an inverted u-tube located within the third chamber above a bottom of the third chamber; (iii) rising liquid within the third chamber forces liquid into a first submerged end of the inverted u-tube and concurrently aspirating air from the second low end of the inverted u-tube located below the bottom of the third chamber; (iv) liquid fills the third chamber to submerge the entirety of the inverted u-tube initiating a flow of liquid from the submerged first high end of the u-tube to a second low end of the u-tube creating a negative pressure at the first end of the u-tube; (v) a volume of liquid can be rapidly drawn from the third chamber until the high end of the u-tube can no longer be submerged and the pressure can be equalized at both ends of the u-tube, (e.g., the u-tube is emptied), initiating a subsequent fill/discharge cycle; (vi) an elapsed time to fill and/or discharge the third chamber of known volume can be determined; and (vii) a flow rate of excommunicating liquid from the second chamber can be determined as the volume of liquid discharged by the u-tube divided by the time interval needed to fill and/or discharge the volume to a predetermined level within the third chamber.

Embodiments of the present invention can further include a method whereby a standard error of a turbidimeter can be reduced by a correlation of one or more of the sample conditions, for instance temperature, pressure, and/or flow rate, to interference due to fine entrained gas bubbles by altering a determination step(s) of a turbidity assay in response to carry potential and/or outgas potential of the liquid sample.

Embodiments of the present invention can enact an alteration to measurement step(s) and/or determination step(s) of an assay process in correlation with one or more variables including, but not limited to, flow rate, temperature, and pressure. The alterations can be implemented to improve a detection limit of the liquid assay and to verify that a turbidity measuring device is operating at a flow rate within a prescribed operational range.

Provisional application 62/174,243, filed on Jun. 11, 2015, titled "BACKSCATTER REDUCTANT ANAMORPHIC BEAM SAMPLER" and having the same inventor as the current application, is hereby incorporated in its entirety by reference. Provisional application 62/173,101, filed on Jun. 9, 2015, titled "DEAERATOR APPARATUS FOR LIQUID ASSAY" and having the same inventor as the current application, is hereby incorporated in its entirety by reference. Provisional application 62/244,004, filed on Oct. 20, 2015, titled "Device for Removing Beam Energy from a Liquid and a Method of Use Thereof" and having the same inventor as the current application, is hereby incorporated in its entirety by reference. PCT application PCT/US16/36202, filed on Jun. 7, 2016, titled "BACKSCATTER REDUCTANT ANAMORPHIC BEAM SAMPLER" and having the same inventor as the current application, is hereby incorporated in its entirety by reference. PCT application PCT/US16/35638, filed on Jun. 3, 2016, titled "TURBIDITY MEASURING DEVICE" and having the same inventor as the current application, is hereby incorporated in its entirety by reference. PCT application PCT/US16/57852, filed on Oct. 20, 2016, titled "Device for Removing Beam Energy from a Liquid and a Method(s) of Use Thereof" and having the same inventor as the current application, is hereby incorporated in its entirety by reference.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment", "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of a applicable element or article, and are used accordingly to aid in the description of the various embodiments and are not necessarily intended to be construed as limiting.

An Embodiment of a Turbidity Measuring Device

Referring to FIG. 1, an embodiment 100 of a turbidity measuring device is illustrated. In one example, the turbidity measuring device can be a turbidimeter. As can be appreciated, the turbidity measuring device may be, but is not limited to, a turbidimeter, a nephelometer, a fluorimeter, or a similar assay device.

Figure 2:
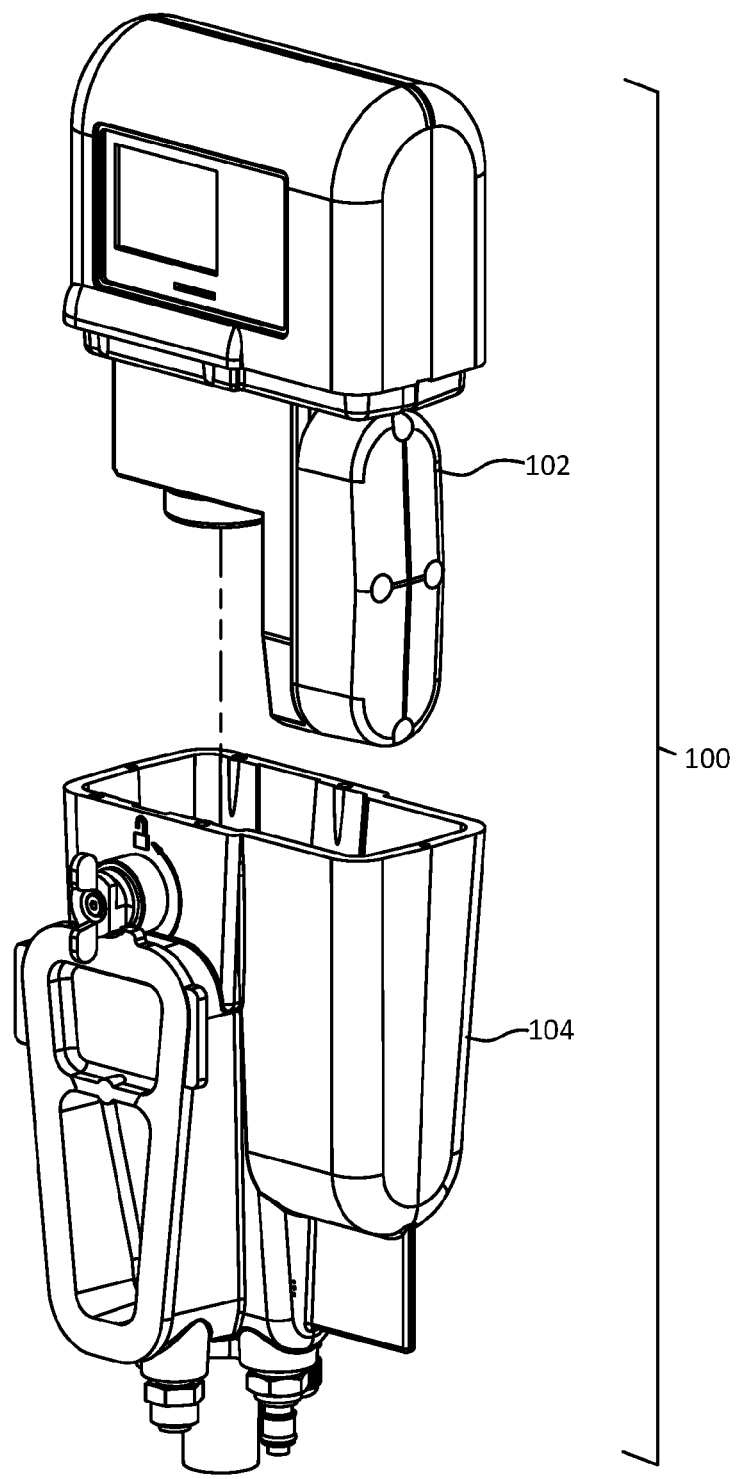
FIG. 2 is an exploded view of a turbidity measuring device according to one embodiment of the present invention.

Referring to FIG. 2, an exploded view of the turbidimeter 100 is illustrated. Typically, the turbidimeter 100 can include a measurement module 102 and a fluidic module 104. The measurement module 102 can be implemented to project a beam of interrogating light, or other non-visible electromagnetic radiation, into a liquid sample located in a chamber of the fluidic module 104. The measurement module 102 can detect an amount of light scattered by particulate matter suspended within the liquid sample. In one instance, detection means of the measurement module 102 can be located at approximately 90 degrees in relation to a path of the interrogation beam at a predefined depth within the liquid sample. The amount of scattered light can be correlated by comparison to a known turbidity standard, such as Formazin, so that an assay of the concentration of particulate matter contained within the sample may be determined in units of Nephelometric Turbidity Units (NTU) and/or Formazin Nephelometric Units (FNU).

As shown, the measurement module 102 can be configured to nest within the fluidic module 104. When the measurement module 102 is assembled with the fluidic module 104, the turbidimeter 100 can be in an operating configuration. In an operating configuration, a detection apparatus of the measurement module 102 can be configured to be immersed within a liquid and an illumination apparatus can project a beam of light, or other invisible beam of electromagnetic radiation, into the liquid sample from above a surface of the liquid.

Figure 3:
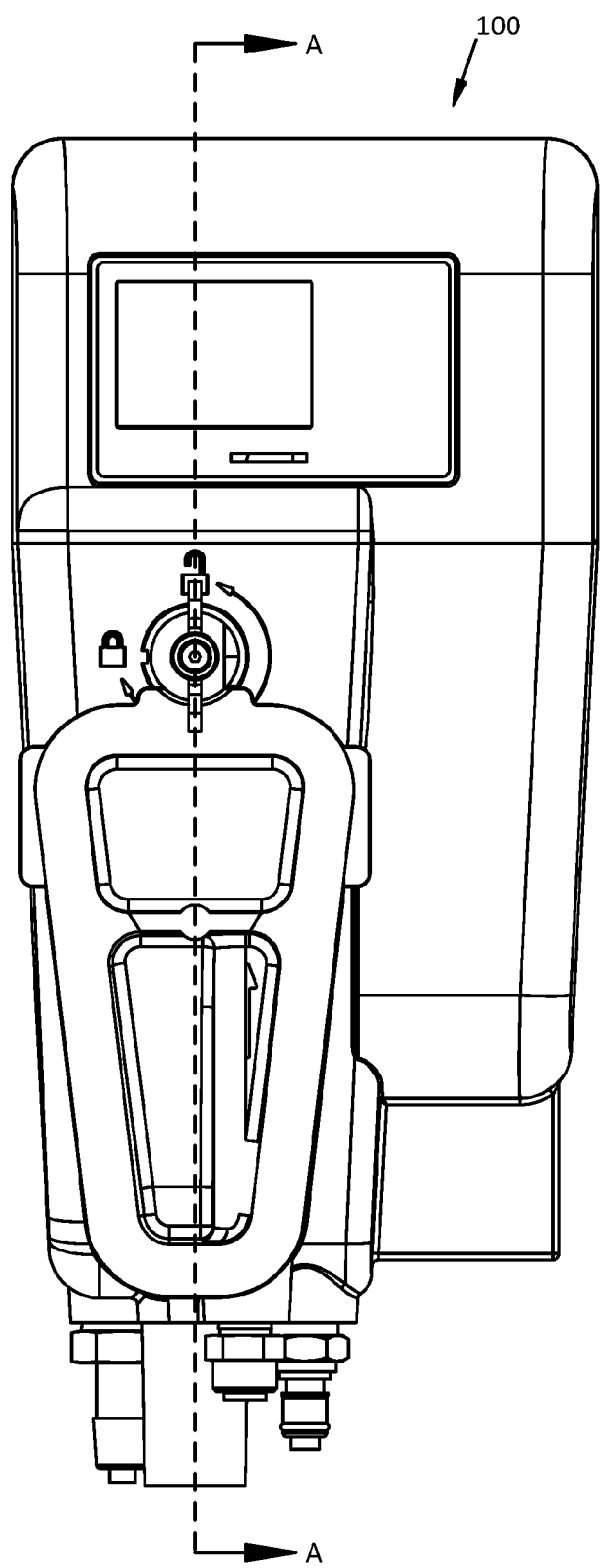
FIG. 3 is a front view of a turbidity measuring device showing cross-section line A-A according to one embodiment of the present invention.

Referring to FIG. 3, a front view of the turbidimeter 100 showing a cross-sectional line A-A is illustrated.

Figure 4:
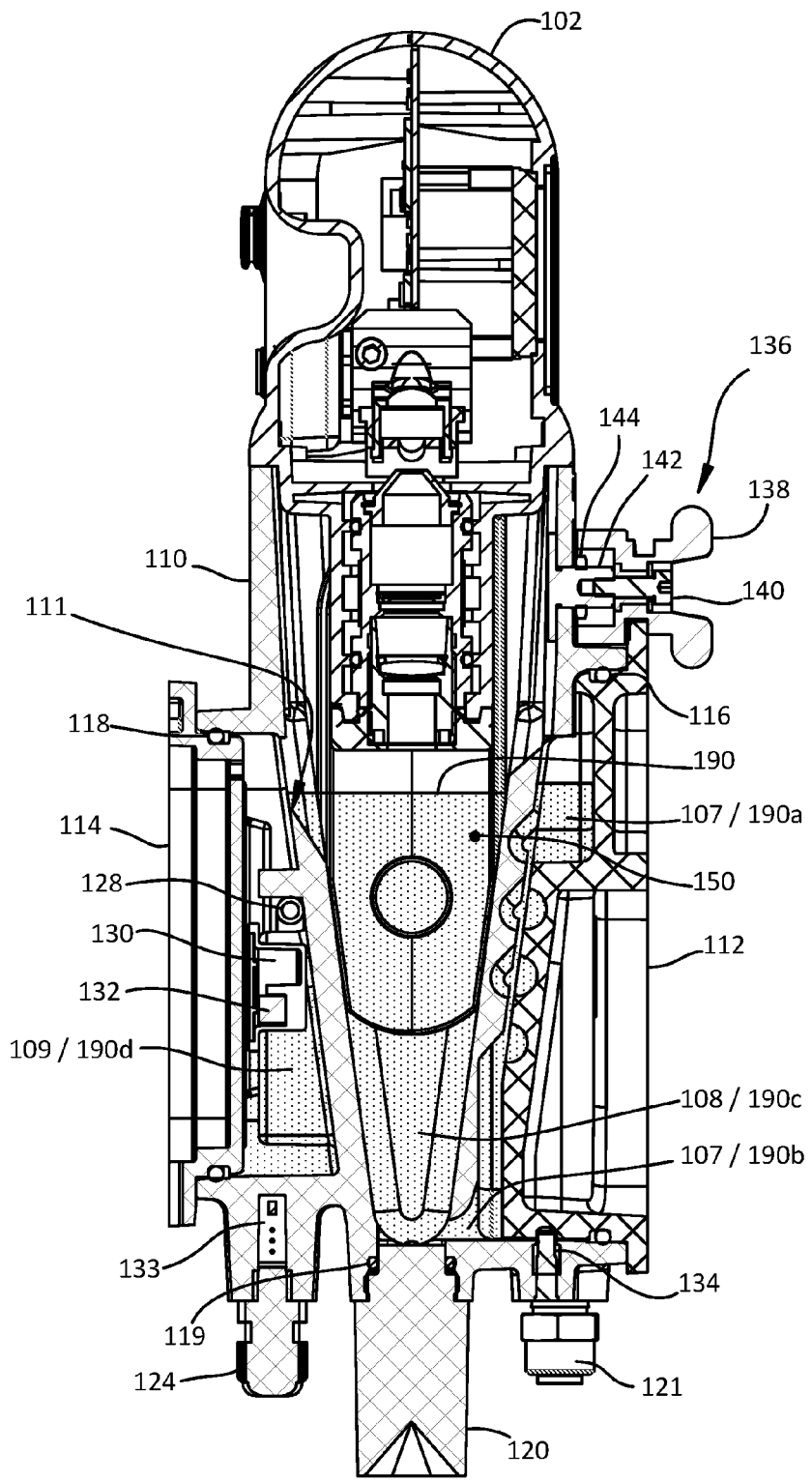
FIG. 4 is a cross-section view taken along line A-A in FIG. 3 of the turbidity measuring device according to one embodiment of the present invention.

Referring to FIG. 4, a cross-sectional view of the turbidimeter 100 along the line A-A is illustrated. In one embodiment, the fluidic module 104 can be divided into a plurality of chambers. Typically, each of the chambers can be configured to be in communication with a portion of a liquid sample. A first chamber 107 can be implemented as an inlet/flow-down chamber, a second chamber 108 can be implemented as a measurement chamber, and a third chamber 109 can be implemented as an outlet/flow measurement chamber. Hereinafter, the first chamber 107 will be referred to as the deaerator chamber, the second chamber 108 will be referred to as the measurement chamber, and the third chamber 109 will be referred to as the waste chamber. The deaerator chamber 107 can be in fluid communication with the measurement chamber 108 and the measurement chamber 108 can be in fluid communication with the waste chamber 109.

Figure 5:
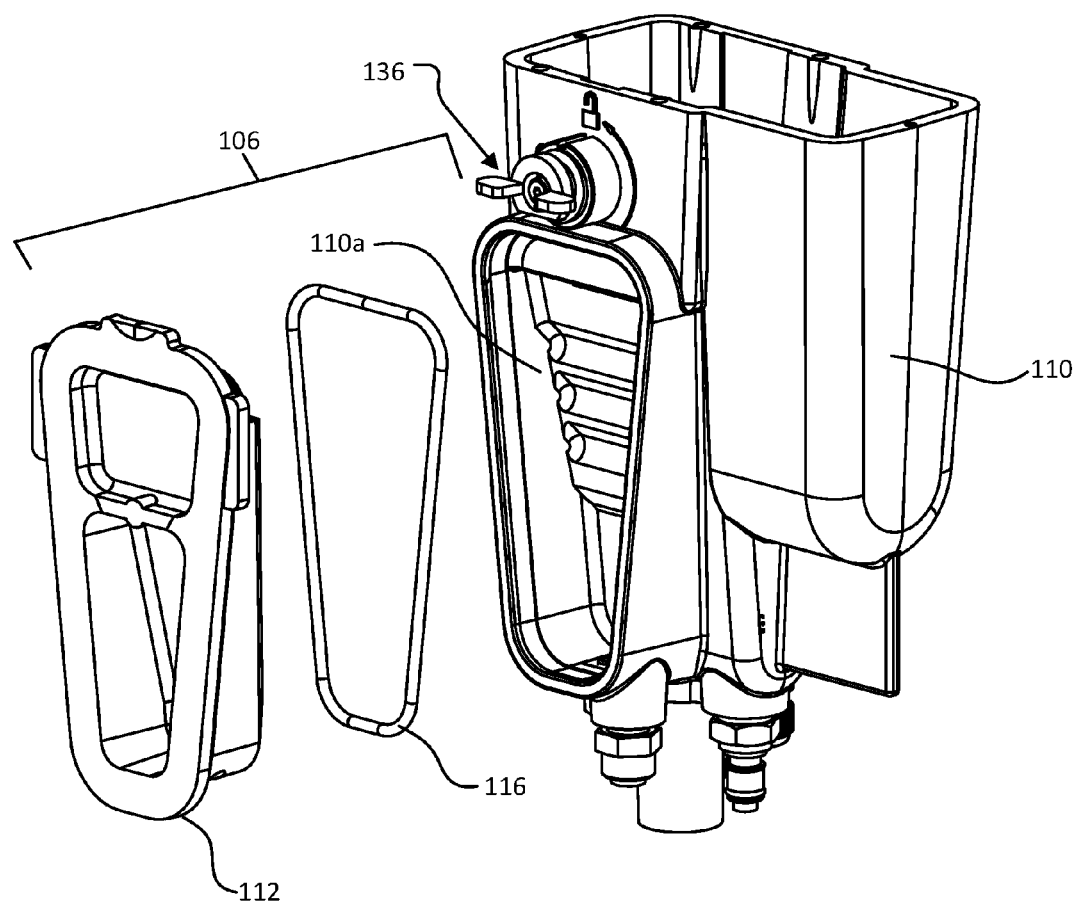
FIG. 5 is an exploded view of a fluidic module assembly according to one embodiment of the present invention.

Referring to FIG. 5, an exploded view of a front of the fluidic module 104 is illustrated. As shown, the fluidic module 104 can include, but is not limited to, a flow body 110, a flow guide cover 112, and a flow guide seal 116. Generally, the fluidic module 104 can include a deaerator to remove entrained air or gas bubbles from the liquid sample being assayed. For instance, a sub-assembly 106 of the fluidic module 104 can be implemented to deaerate a liquid sample. The sub-assembly 106 can generally include a flow cavity 110a of the flow body 110, the flow guide cover 112, and the flow guide seal 116. As shown in FIG. 5, an interior side of the flow guide cover 112 can be partially inserted into the flow cavity 110a of the flow body 110. Stated alternatively, the flow cavity 110a can be configured to receive and mate with the flow guide cover 112.

Figure 6:
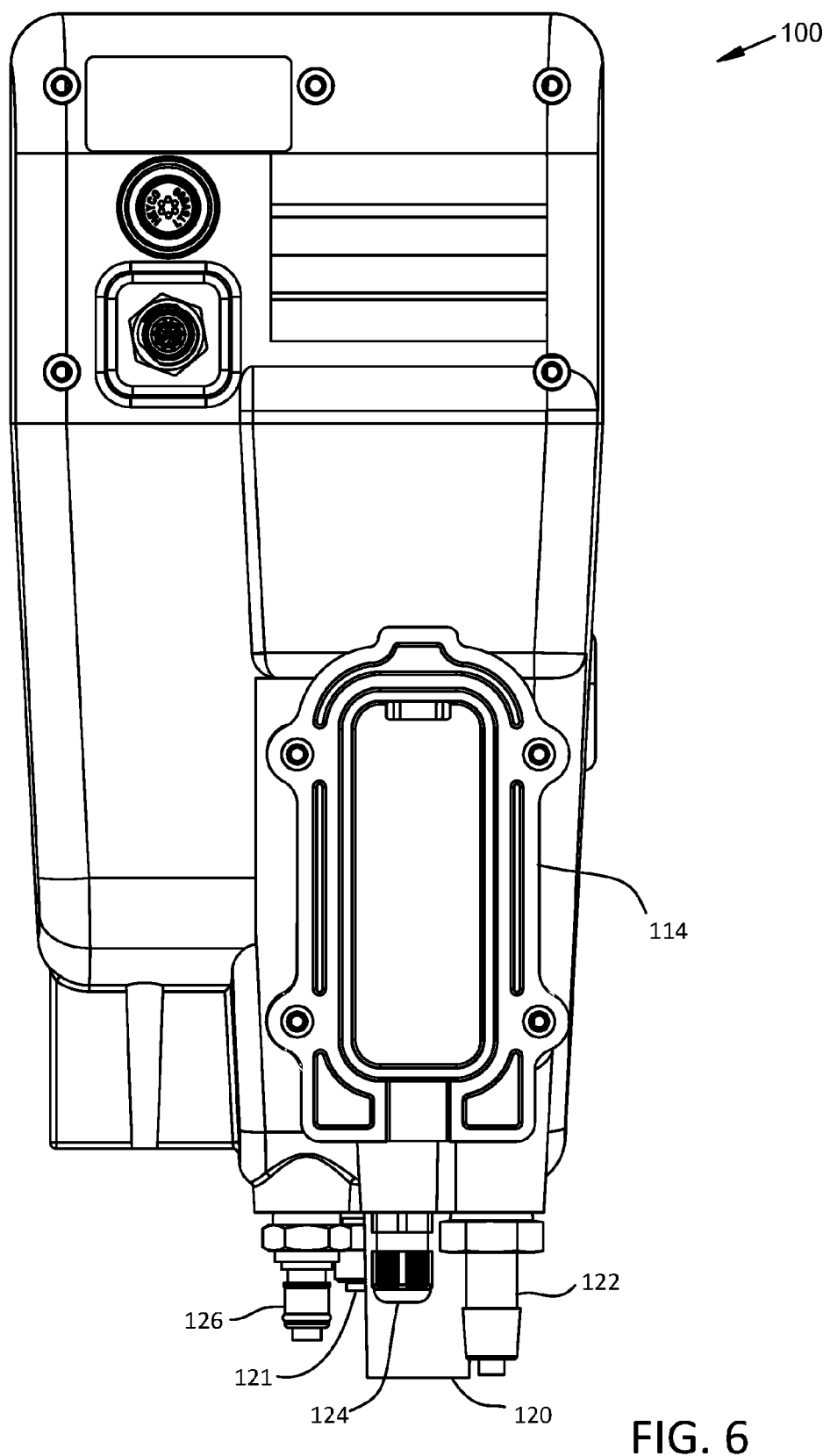
FIG. 6 is a back view of a turbidity measuring device according to one embodiment of the present invention.

Referring to FIG. 6, a back view of the turbidimeter 100 is illustrated. As shown, the fluidic module 104 can further include a back cover 114, a back cover seal 118 (shown in FIG. 7), a beam dump 120, an inlet fitting 121, an outlet fitting 122, a cable gland 124, and a quick-disconnect fitting 126. The quick-disconnect fitting 126, typically located at the lowest point of liquid containment within the flow body 110 of the fluidic module 104, can incorporate a check-valve to facilitate a transfer of liquid to or from the flow body 110 when a connection is made to the quick-disconnect fitting 126. The transfer of liquid in and out of the flow body 110 can be useful when a calibration sample or a standard of known concentration or turbidity is to be introduced into the measurement chamber 108 without disassembly of the turbidimeter 100.

Figure 7:
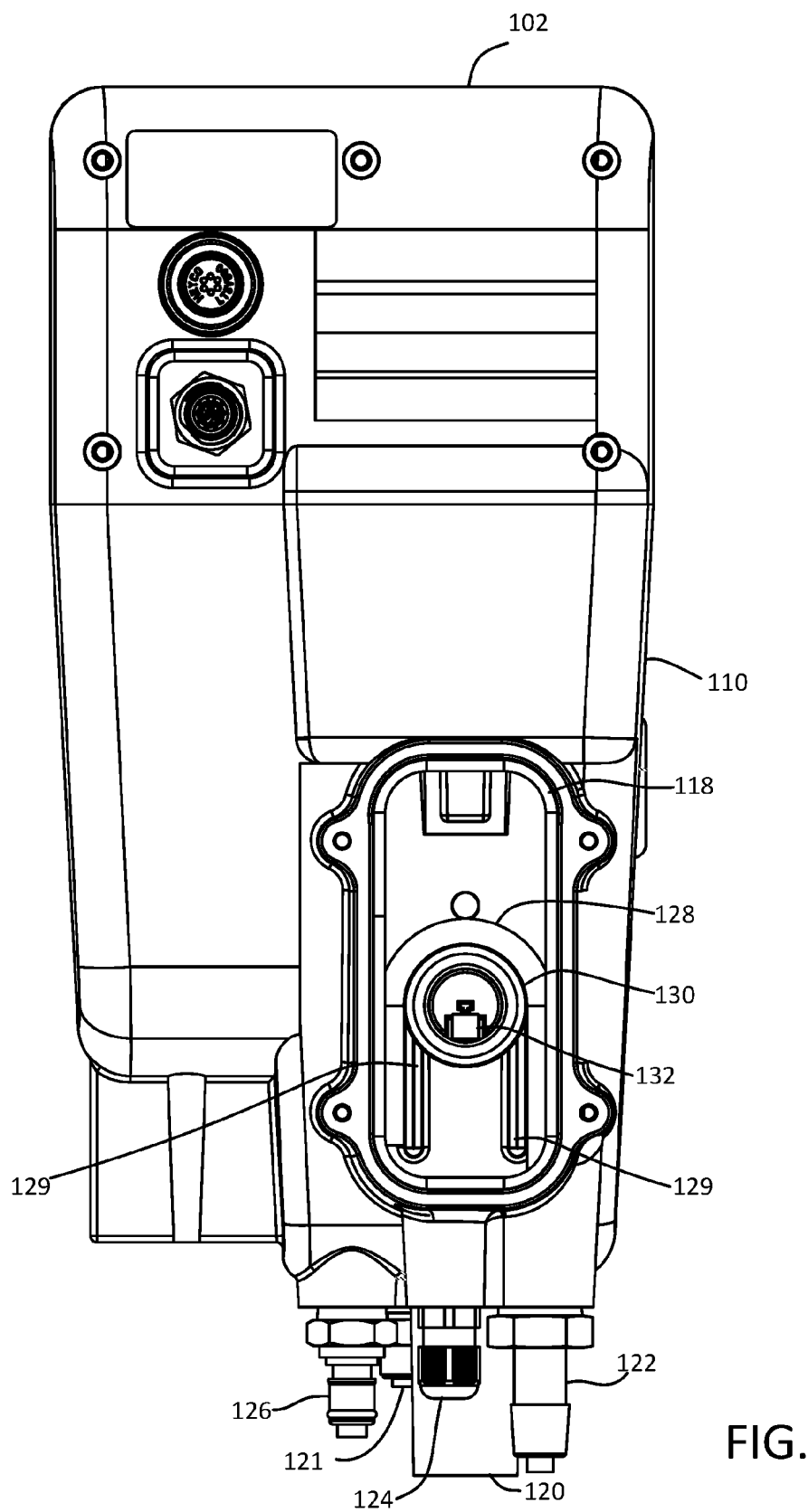
FIG. 7 is a back view of a turbidity measuring device with a back cover removed according to one embodiment of the present invention.

Referring to FIG. 7, a back view of the turbidimeter 100 is shown with the back cover 114 removed. As shown, the fluidic module 104 can further include a siphon tube 128, a float 130, a magnet 132, and the back cover seal 118. As shown, the magnet 130 can typically be located within, or housed in, the float 130.

Referring back to FIG. 4, a liquid sample 190 can be located throughout the turbidimeter 100. As can be appreciated, the liquid sample 190 can be introduced to the turbidimeter 100 via the inlet fitting 121. While in the turbidimeter 100, reference to the liquid sample 190 will be based on a location of the liquid sample 190 in the turbidimeter 100. For instance, when the liquid sample 190 first enters the turbidimeter 100 and is being deaerated, the liquid sample 190 will be referred to as the non-deaerated liquid sample 190a. After the liquid sample 190 has been deaerated and is located in the deaerator chamber 107, the liquid sample 190 will be referred to as the deaerated liquid sample 190b. When the liquid sample 190 is located in the measurement chamber 108, the liquid sample 190 will be referred to as the assay liquid sample 190c. The liquid sample 190 located in the waste chamber 109 will be referred to as the waste liquid sample 190d. The deaerated liquid sample 190b can flow into the measurement chamber 108 of the flow body 110 occupied by an assay liquid sample 190c. For instance, the deaerated liquid sample 190b can flow through an opening at a bottom of the flow body 110 between the deaerator chamber 107 and the measurement chamber 108.

In one embodiment, the flow guide cover 112 can be coupled to the fluidic module 104 by a pin 134 and a retaining latch assembly 136. As shown, the retaining latch assembly 136 can include a wing nut 138, a shoulder bolt 140, a panel bolt 142, and a panel nut 144.

In one embodiment, the fluidic module 104 can further include a temperature sensor 150, as shown in FIG. 4. Typically, the temperature sensor 150 can be located within the measurement chamber 108 of the fluidic module 104. The temperature sensor 150 can be implemented to measure a temperature of the liquid sample 190 during an assay process. In a typical implementation, the assay liquid sample 190c can flow upward in the measurement chamber 108 during which the assay liquid sample 190c can be interrogated by a beam of light projected downward from the measurement module 102 through the assay liquid sample 190c to the beam dump 120. The beam dump 120 can be made leak-tight when coupled to the flow body 110 by a beam dump seal 119. Light that is scattered or is otherwise redirected as result of the process of photoluminescence, fluorescence, or other optical phenomenon, can fall incident upon a detector means of the measurement module 102, at substantially a right angle to the interrogation beam. The light energy can be converted to an electrical signal by the detector means of the measurement module 102 in proportion to a particle concentration within the assay liquid sample 190c. The light energy can further be quantized by the measurement module 102 as a measured value.

In an example implementation of the turbidimeter 100, a liquid sample 190 can flow upward from the inlet fitting 121 to the deaerator chamber 107. As shown, the deaerator chamber 107 can be formed by a space between the flow guide cover 112 and the flow body 110, as shown being occupied by the non-aerated liquid sample 190a. The flow guide cover 112 can be made leak-tight when coupled to the flow body 110 by a flow guide seal 116. The non-aerated liquid sample 190a can flow downward across structures in the flow body 110 and the flow guide cover 112 to substantially remove entrained gases bubbles from the non-aerated liquid sample 190a. A deaerated liquid sample 190b can be produced when the non-aerated liquid sample 190a flows downward across the structures in the flow body 110 and the flow guide cover 112.

The assay liquid sample 190c can overflow a weir 111 (shown in FIGS. 4 and 11) at a top of the flow body 110 from the measurement chamber 108 into the waste chamber 109. A volume of the waste chamber 109 can be defined by a space between the back cover 114 and the flow body 110 being occupied by the waste liquid sample 190d. The back cover 114 can be made leak-tight when coupled to the flow body 110 by the back cover seal 118.

Figure 8:
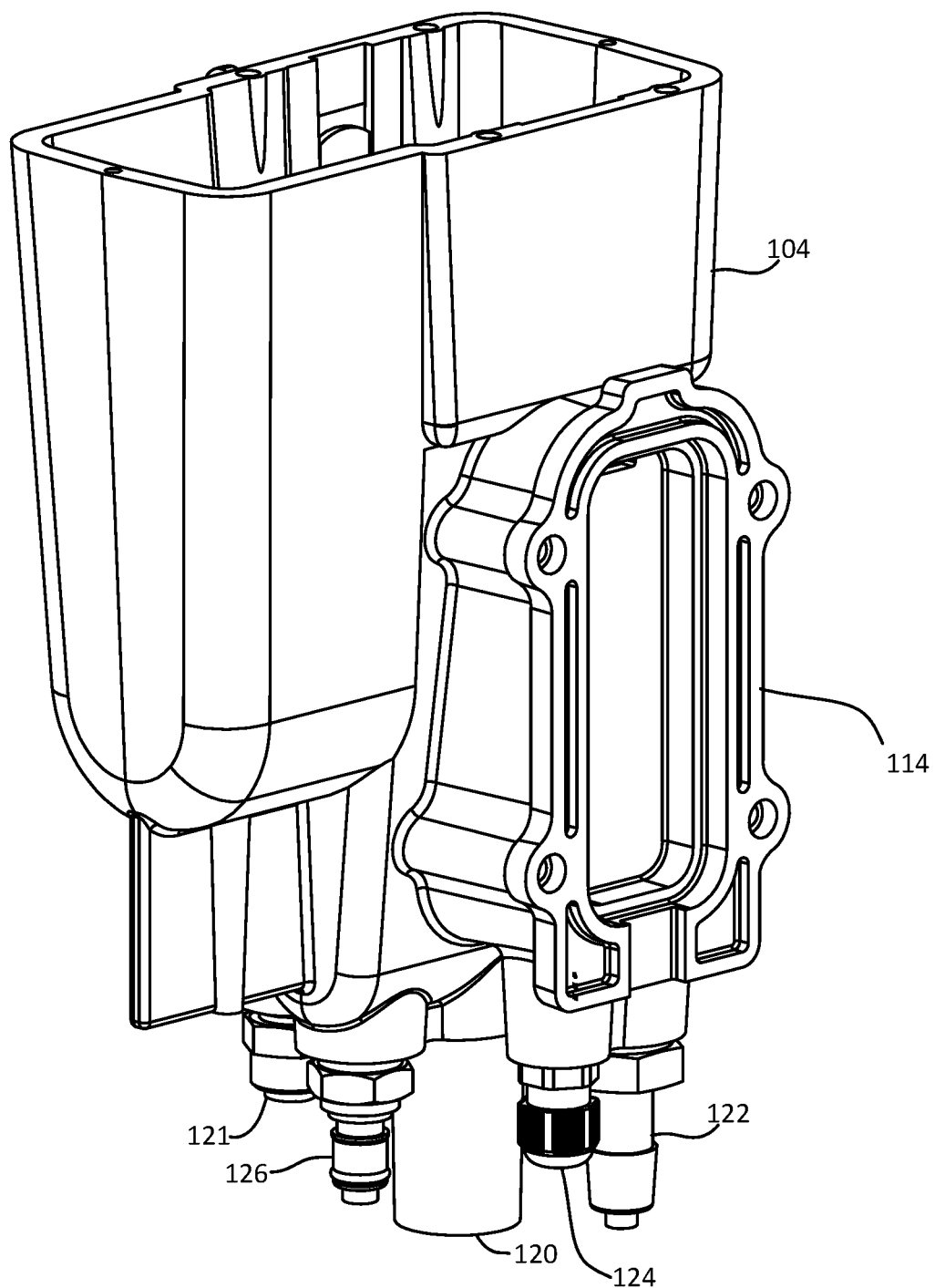
FIG. 8 is a back isometric view of a fluidic module assembly according to one embodiment of the present invention.

Referring to FIG. 8, an isometric view of the back of the fluidic module 104 is illustrated.

Figure 9:
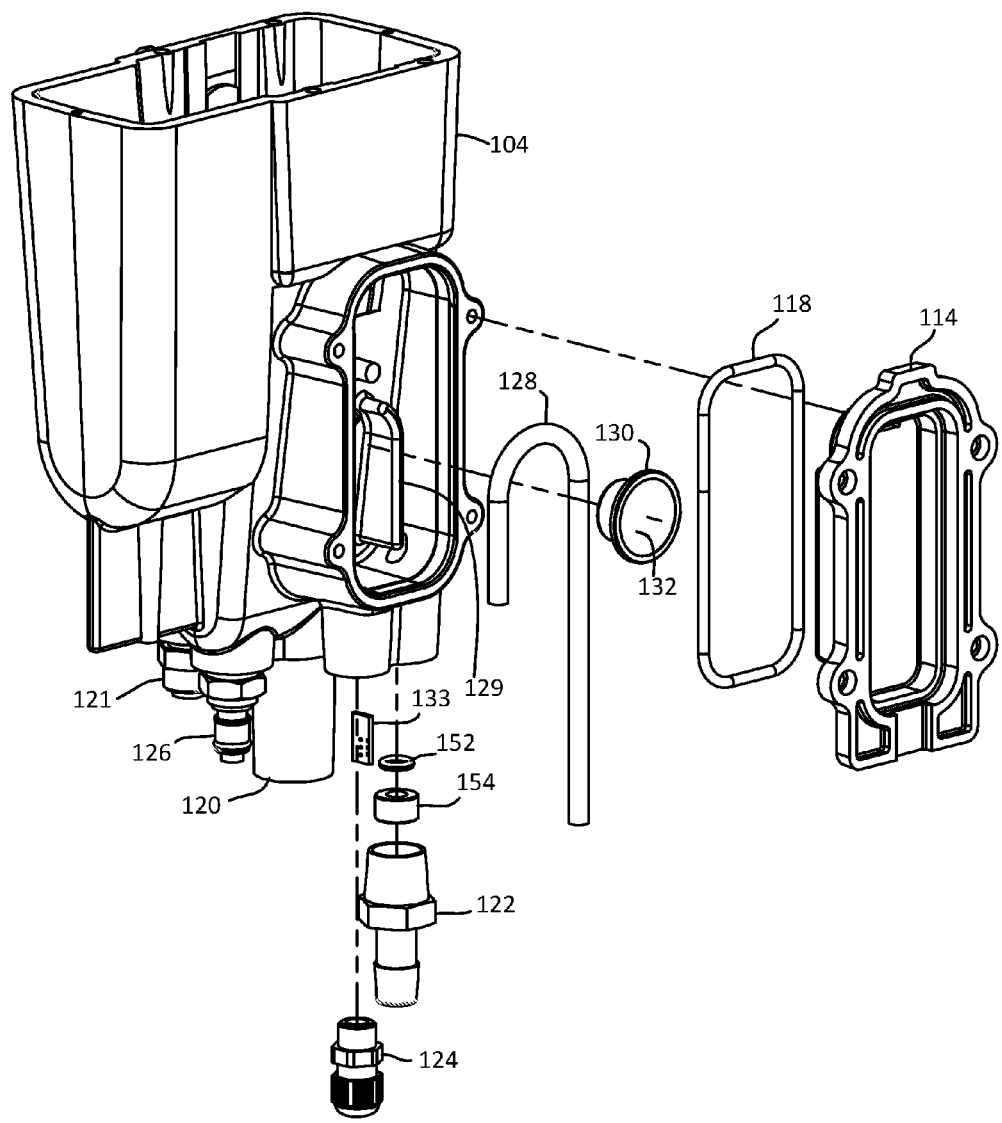
FIG. 9 is an exploded view of a fluidic module assembly according to one embodiment of the present invention.

Referring to FIG. 9, an exploded view of the back of the fluidic module 104 is illustrated. In one embodiment, the siphon tube 128 can be formed into an inverted U-shaped tube by one or more constraining features 129 of the flow body 110 located within the waste chamber 109. As can be appreciated, the constraining features 129 can otherwise act as vertical guide members for the float 130 and can constrain movement of the float 130 to move vertically between the guide members 129 and the back cover 114. The magnet 132 can be located within the float 130, typically biased with the magnetic poles of the magnet 132 oriented substantially perpendicular and tangent to an inside perimeter defined by the guide members 129. As a result, when the assembly of the float 130 and the magnet 132 are in free-float, the weight of the magnet 132 may cause the float 130 to rotate to a position where the magnetic poles of the magnet 132 are aligned vertically and the magnet 132 can be in a position closest to a bottom of the waste chamber 109 within the vertical guide members 129 of the flow body 110.

As shown in FIG. 9, a lower portion of the siphon tube 128 can be made leak-tight when coupled to the flow body 110 by an o-ring seal 152, a compression bushing 154, and the outlet fitting 122. Typically, the siphon tube 128 can be inserted into the flow body 110 through the outlet fitting 122, the compression bushing 154, and the O-ring seal 152.

Figure 10:
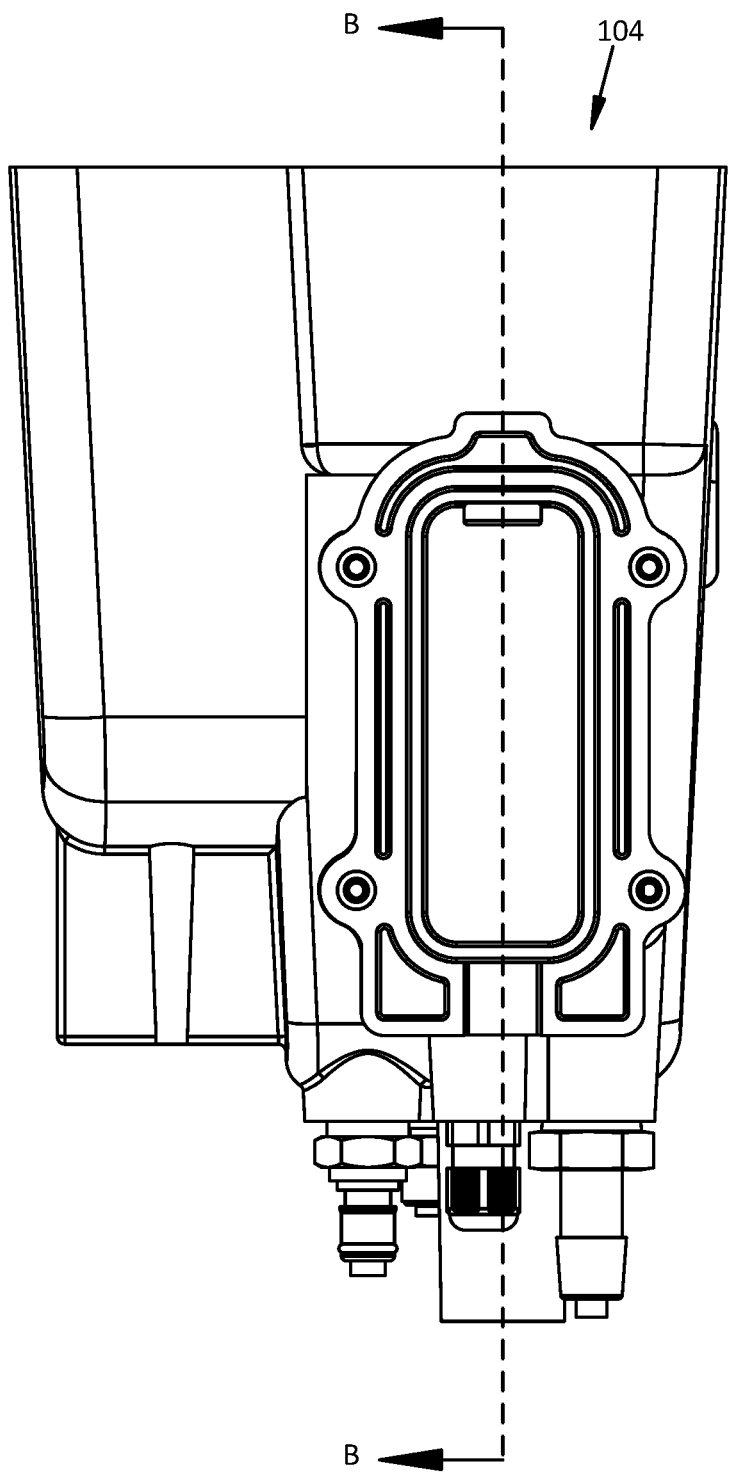
FIG. 10 is a back view of a fluidic module assembly showing cross-section line B-B according to one embodiment of the present invention.

Referring to FIG. 10, a front view of the fluidic module 104 showing a cross-sectional line B-B is illustrated.

Figure 11:
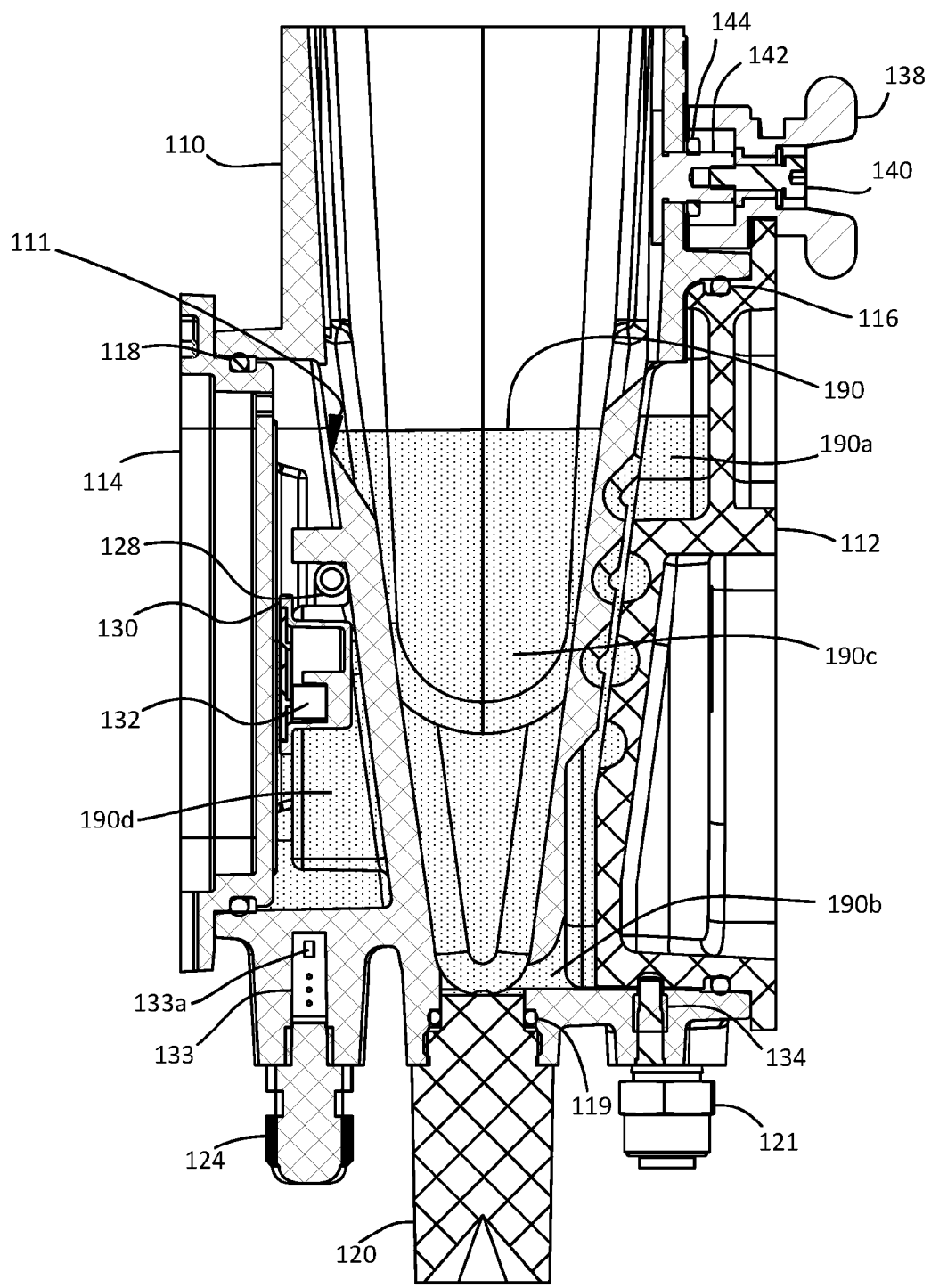
FIG. 11 is a cross-section view of line B-B in FIG. 9 of the fluidic module assembly according to one embodiment of the present invention.

Referring to FIG. 11, a cross-sectional view of the fluidic module 104 along the line B-B is illustrated. As shown, the fluidic module 104 can include a magnetic sensor assembly 133 fixed to the flow body 110. Typically, the magnetic sensor assembly 133 can include a magnetic sensor 133a for interfacing with the magnet 132. The magnetic sensor assembly 133 can typically be oriented vertical and collinear with the magnetic poles of the magnet 132 when the float 130 is free-float oriented. In one embodiment, the magnetic sensor assembly 133 can be fixed in position to the flow body 110 by the cable gland 124. A separation distance between the float 130 and the magnetic sensor assembly 133 can be altered in accordance to a height of liquid within the waste chamber 109.

As shown in FIG. 11, the separation distance between the magnet 132 and the magnetic sensor 133a can be greatest when the waste liquid sample 190d is of sufficient volume to cause the vertical guide members 129 of the flow body 110 to stop an ascent of the float 130.

Figure 12:
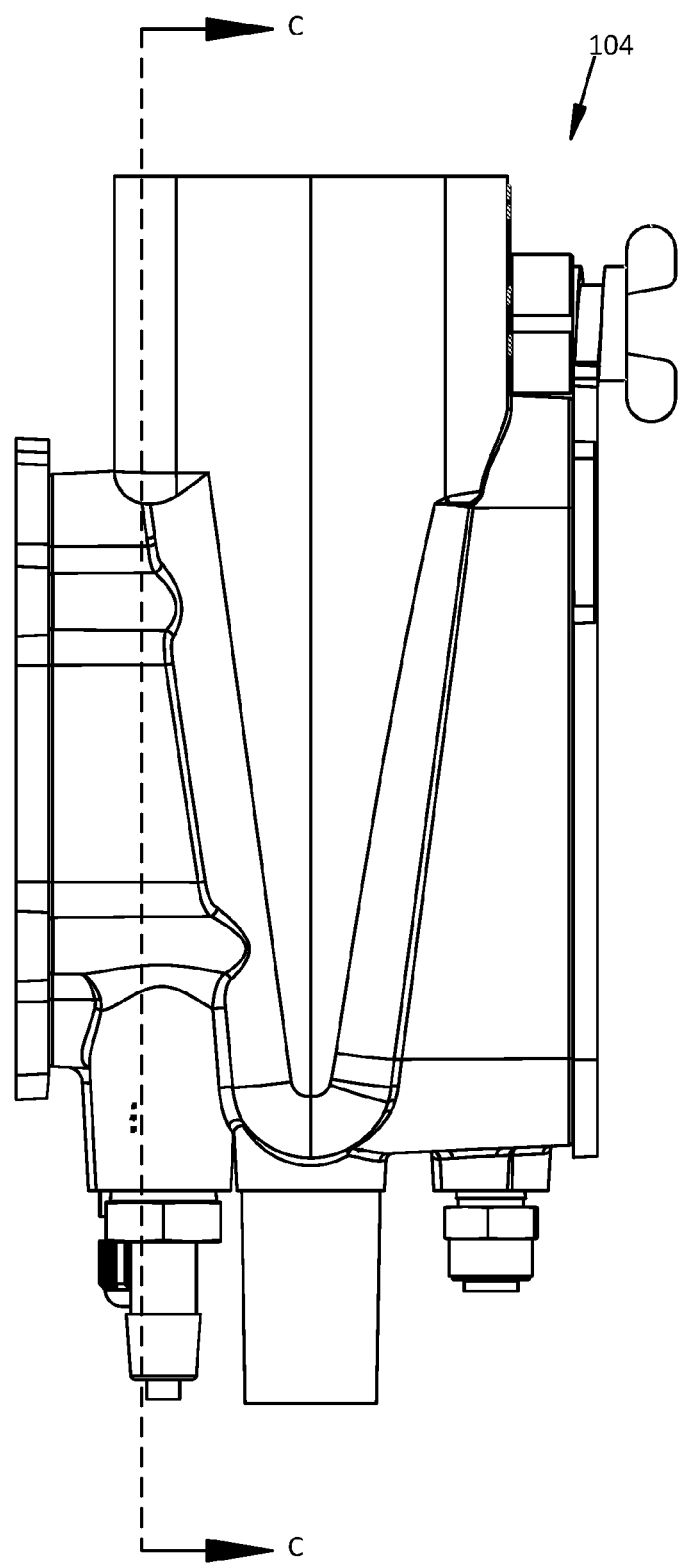
FIG. 12 is a side view of a fluidic module assembly showing cross-section line C-C according to one embodiment of the present invention.

Referring to FIG. 12, a side view of the fluidic module 104 showing a cross-sectional line C-C is illustrated.

Figure 13:
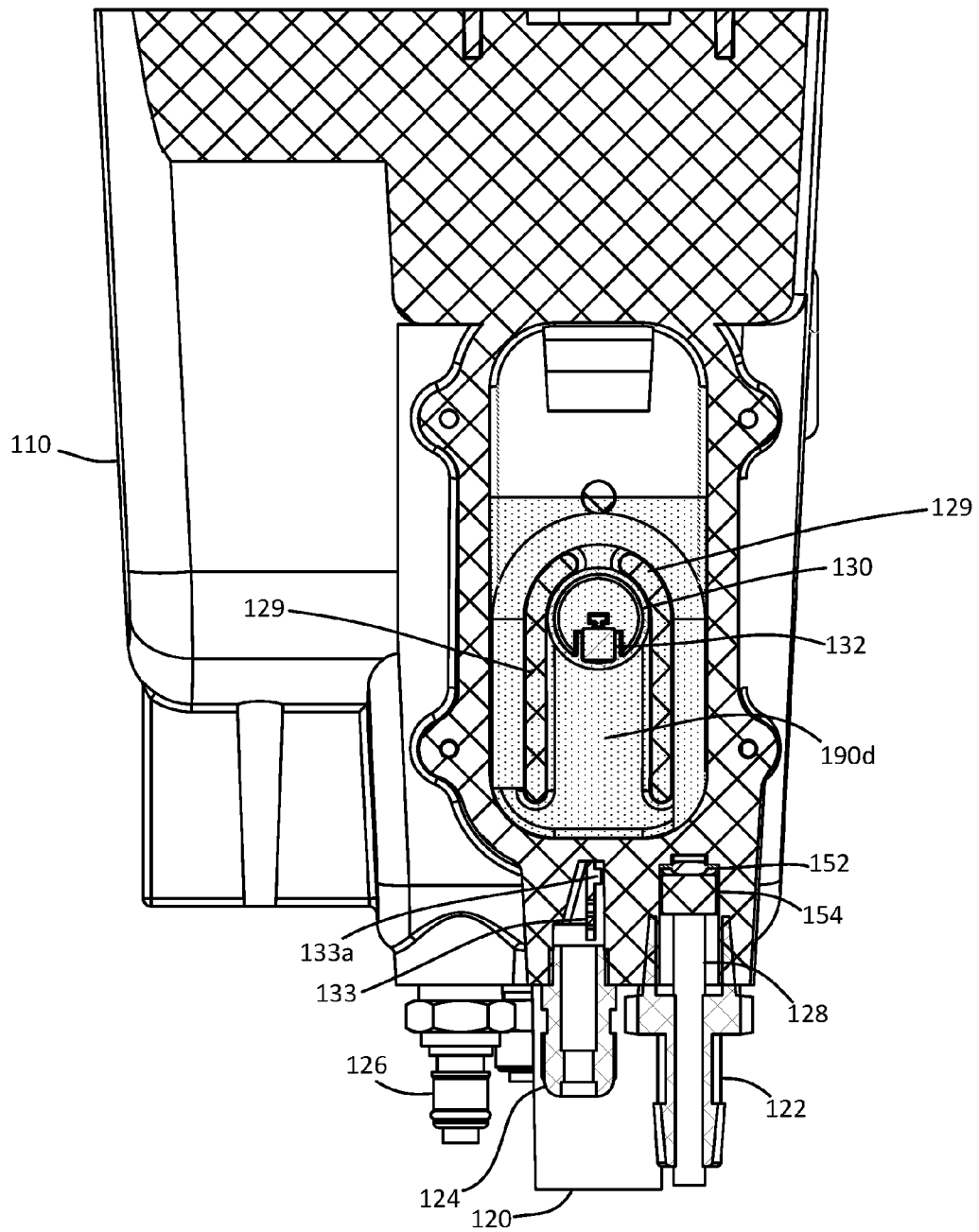
FIG. 13 is a cross-section view of line C-C in FIG. 11 of the fluidic module assembly according to one embodiment of the present invention.

Referring to FIG. 13, a cross-sectional view of the fluidic module 104 along the line C-C is illustrated. As shown in FIG. 13, liquid can continue to fill the waste chamber 109 with the waste liquid sample 190d to beyond a height of the siphon tube 128 to a tipping point. The tipping point can occur when a pressure caused by a height of the liquid of a submerged end of the siphon tube 128 can be sufficient to surpass static forces within the siphon tube 128 and atmospheric pressure at an opposing end of the siphon tube 128 resulting in flow within the siphon tube 128. The vertical guide members 129 are shown restricting the float 130 from floating to a top of the liquid in the waste chamber 109.

To advantage, the waste chamber 109 can fill by way of an overflow across the weir 111 allowing the surface of the assay liquid sample 190c to remain free of ripples so as not to induce perturbations in the cross-sectional energy density of the interrogation beam. As the waste chamber 109 fills with the waste liquid sample 190d, the float 130 containing the magnet 132 can move upward away from a magnetic sensor assembly 133. A logic signal can be generated by the magnetic sensor assembly 133 based upon the proximity of the magnet 132 to the magnetic sensor 133a. The logic signal can be communicated to the measurement module 102 through a cable connected to the flow body 110 at the cable gland 124.

Once the waste chamber fills to a level above the siphon tube 128, as shown in FIG. 13, an evacuation cycle may commence. The evacuation cycle may include, but is not limited to, the steps of: (i) the waste liquid 190d can be drawn out of the waste chamber 109 through the siphon tube 128 due to negative pressure created by a flow of the waste liquid 190d to a drain; (ii) the float 130 containing the magnet 132 can fall to the bottom of the waste chamber 109; and (iii) the fall of the float 130 can be detected by the magnetic sensor assembly 133. The float 130 can generally rise and fall at a frequency proportional to a flow of a liquid through the turbidimeter 100.

Figure 14:
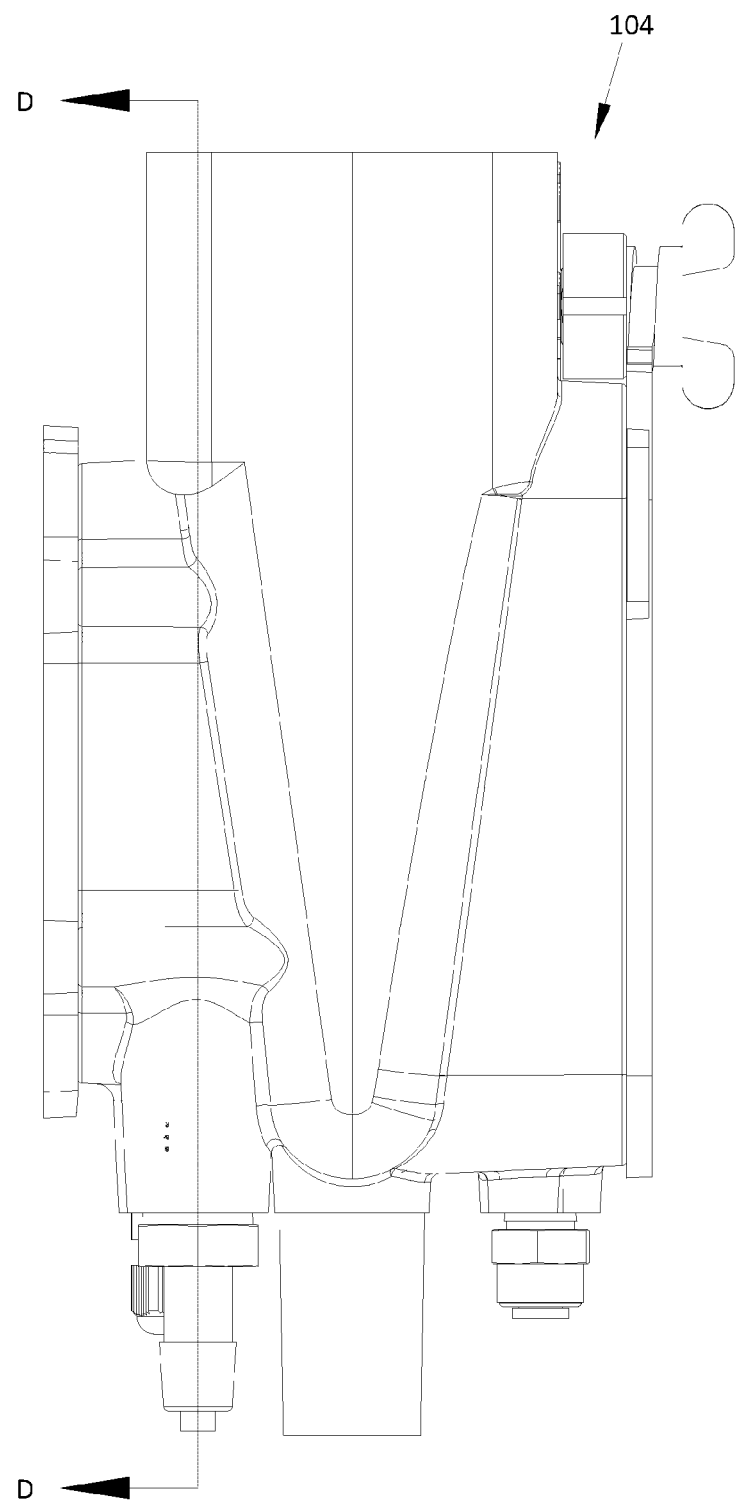
FIG. 14 is a side view of a fluidic module assembly showing cross-section line D-D according to one embodiment of the present invention.

Referring to FIG. 14, a side view of the fluidic module 104 showing a cross-sectional line D-D is illustrated.

Figure 15:
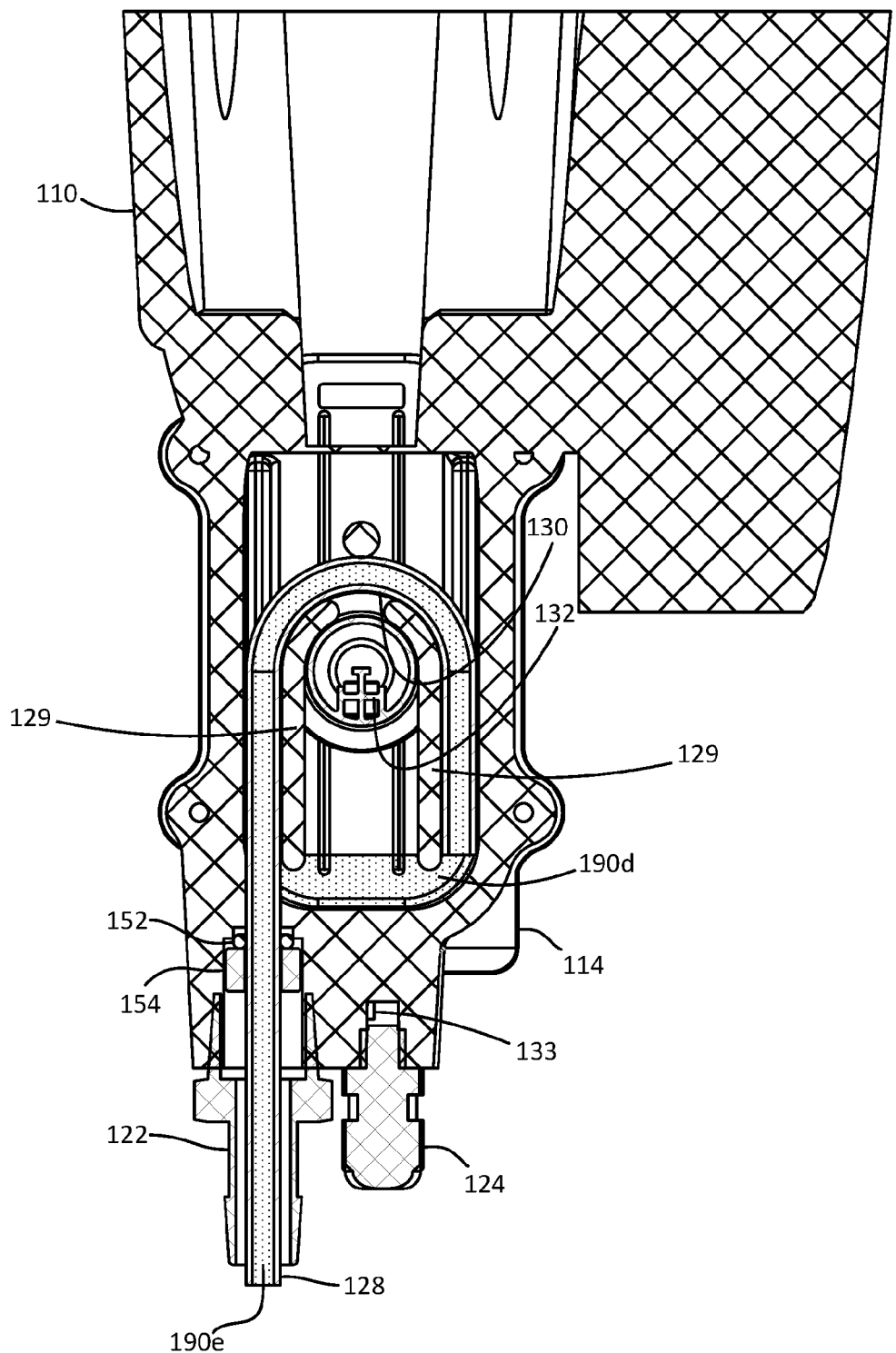
FIG. 15 is a cross-section view of line D-D in FIG. 13 of the fluidic module assembly according to one embodiment of the present invention.

Referring to FIG. 15, a cross-sectional view of the fluidic module 104 along the line D-D is illustrated. A flow of the liquid sample 190 within the siphon tube 128, referred to as a liquid sample effluent 190e, can rapidly draw liquid from the waste chamber 109 by means of gravimetric flow permitting the float 130 to fall and communicate with the magnetic sensor 133a. Flow can continue within the siphon tube 128 until pressure is equalized at both ends of the siphon tube 128. For instance, air can be drawn into the once submerged end of the siphon tube 128, as illustrated in FIG. 15. A volume of liquid drawn from the waste chamber 109 for each evacuation cycle can be substantially determined by a volume of the waste chamber 109 as determined by a volume of liquid contained between a bottom of the siphon tube 128 and a maximum height of the siphon tube 128 within the waste chamber 109.

Figure 16:
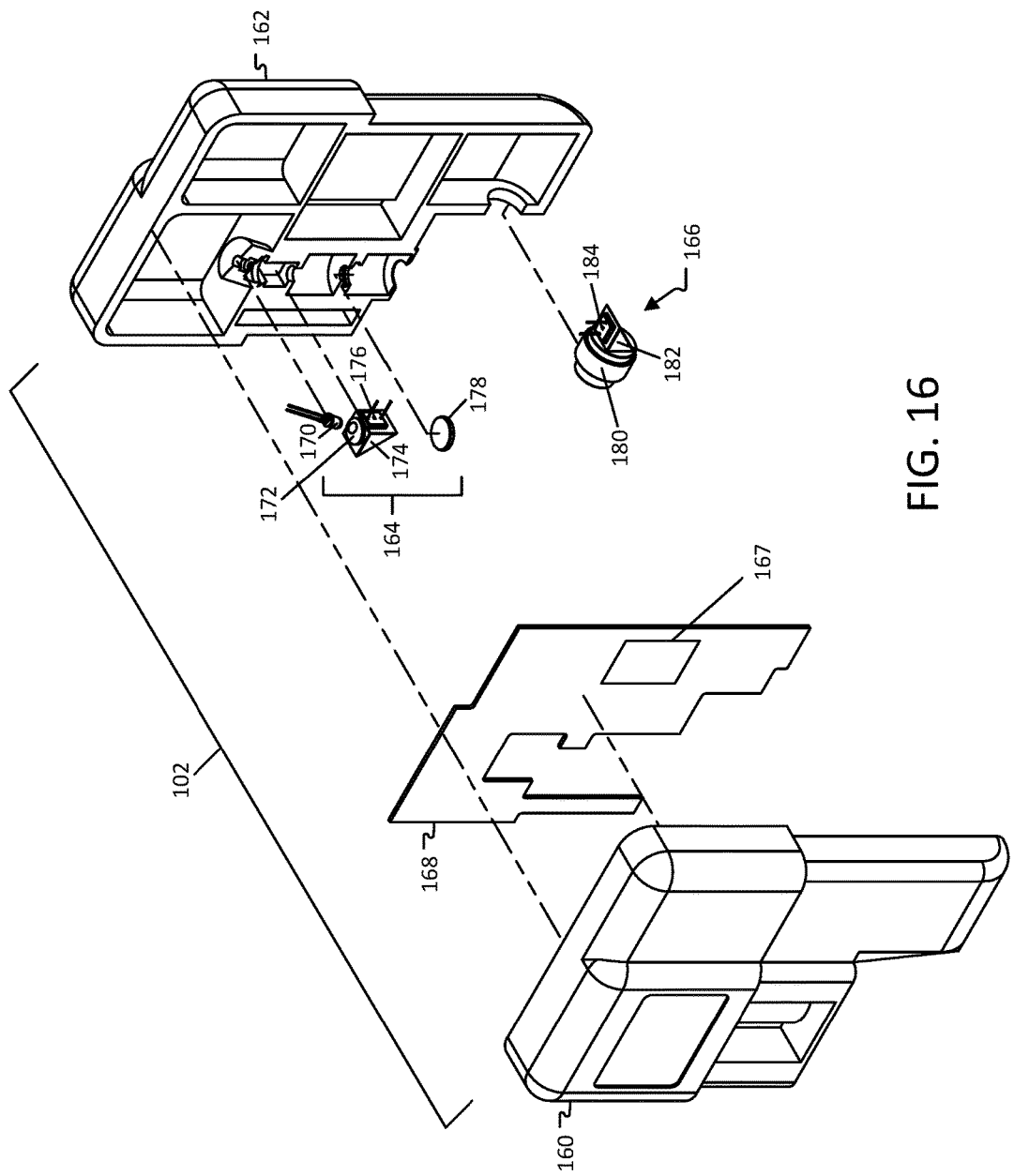
FIG. 16 is an exploded view of a measurement module assembly according to one embodiment of the present invention.

Referring to FIG. 16, an exploded view of the measurement module 102 is illustrated. The measurement module 102 can include, but is not limited to, a front housing 160, a rear housing 162, an illumination apparatus 164, a detection apparatus 166, a pressure sensor 167, and a printed circuit assembly 168. Generally, the front housing 160 and the rear housing can be fixed in relation with the illumination apparatus 164, the detection apparatus 166, and the printed circuit assembly 168 located there between, as shown in FIG. 16. The illumination apparatus 164 and the detection apparatus 166 can be held in relation preferentially for nephelometric assay substantially at 90 degrees per the geometry specified by the US Environmental Protection Agency (USEPA) publication 180.1 and to the geometry specified by ISO 7027-1999 standard for, "Water Quality—Determination of Turbidity".

In one embodiment, the pressure sensor 167 can be a board mounted pressure sensor adapted to be mounted on the printed circuit assembly 168. When the measurement module 102 is operatively connected to the fluidic module 104, the pressure sensor 167 can be implemented to measure a barometric pressure in the second chamber. For instance, the pressure sensor 167 can be vented to atmosphere and measure a barometric pressure in the turbidimeter 100.

When the measurement module 102 is assembled with the fluidic module 104, the turbidimeter 100 can be in an operating configuration. In an operating configuration, the detection apparatus 166 can be configured to be immersed within a liquid and the illumination apparatus 164 can project a beam of light, or other invisible beam of electromagnetic radiation, into the liquid sample from above a surface of the liquid.

Still referring to FIG. 16, the illumination apparatus 164 can typically include, but is not limited to, an emitting source 170, a plano-convex lens 172, a right angle prism 174, a first detector 176, and a field lens 178. Light emitted from the emitting source 170 can be substantially shaped into a beam by the plano-convex lens 172. The beam can be configured to fall incident upon a hypotenuse of the right angle prism 174. When the beam falls incident upon the hypotenuse surface of right angle prism 174, the beam can be partially reflected and otherwise refracted at the hypotenuse surface. The refracted portion of the beam propagating from the hypotenuse surface of the right angle prism 174 can be adjusted by the field lens 178 to modify a divergence of the beam and/or focus the beam to within a view of the detection apparatus 166. The first detector 176 can be positioned upon one base of the right angle prism 174 to receive the partially reflected portion of the beam formed by the plano-convex lens 172. For instance, the plano-convex lens 172 can be positioned at a substantially right angle to the first detector 176 upon a second base of the right angle prism 174. In one embodiment, the plano-convex lens 172 and the first detector 176 can be coupled to the right angle prism 174 by an optical epoxy. In one example, the optical epoxy can be Epoxy Technology no. 301-2.

In one embodiment, the detection apparatus 116 can include, but is not limited to, a collection lens 180, a right angle prism 182, and a second detector 184. The detection apparatus 166 can be implemented to collect and convert light into an electrical response. As can be appreciated, scattered light may result from an interaction of the beam propagating from the field lens 178 of the illumination apparatus 164 with a liquid sample contained within the fluidic module 104. The collection lens 180 can receive light scattered by the liquid sample substantially at 90 degrees from the beam propagating from the field lens 178. Light collected by the collection lens 180 can focus light scattered by the liquid sample through the right angle prism 182 to impinge upon the second detector 184. Electrical communication can be made between to the emitting source 170 and the first and second detectors 176, 184 through the printed circuit assembly 168.

As can be appreciated, the amount of light received by the collection lens 180 is dependent upon an intensity of the beam transmitted through the liquid sample and scatter characteristics of the liquid sample. Independent determination can be made for the transmitted beam energy by the first detector 176 and the scattered energy by the second detector 184. With the beam energy accounted for by incident beam first detector 176, additional changes in the energy determined by scattered light second detector 184 are therefore related to the particle content or scatter characteristics of the sample. For instance, this would apply for a non-absorptive liquid sample like water. Because entrained air or other gases present in the liquid sample scatter light with similar vigor as particulate matter present in the liquid sample, entrained air or gas bubbles act as interferences and therefore should be removed as much as possible prior to assay.

In one embodiment, a flow rate in the turbidimeter 100 can be determined as a dispensed volume of liquid during an evacuation cycle divided by a time interval between evacuation cycles. For example, a dispensed volume of 25 mL every 30 seconds equates to an average flow rate of 50 mL/minute. The time interval between evacuation cycles of the waste chamber 109, or of consequence the presence or absence of liquid within the waste chamber, can be determined using alternate detective means in substitute to a magnet float and magnetic sensor as previously described. Alternate detective means can include, but are not limited to, a total internally reflecting (TIR) optical sensor, a transmittance sensor, a pivot float switch, an ultrasonic emitter and detector, a pressure sensitive tape sensor, a conductivity sensor, and/or a pressure sensor. To advantage, a novel arrangement of a siphon flow sensor integral to the waste chamber of a turbidimeter can be capable of measuring flow rates less than 1 mL/min without fouling due to particulate matter in suspension within a liquid sample.

Of important note, if the liquid sample 190 flow is prevented from flowing through the measurement chamber 108 due to blockage or diversion, the lack of sufficient flow can be detected within the waste chamber 109 and a non-conforming instrument condition can be communicated to initiate an appropriate response to restore loss of flow. For instance, measurements made during loss of flow or a flow rate outside of recommended operating parameters can be considered invalid or subject to scrutiny. Potable water, water considered safe for human consumption, requires a declaration which states that the determination of the quality of the water made during an assay process is unequivocally of the same water that flowed through the turbidity measuring device. A measure of the sample flow using external means does not unarguably associate the assay process and the sample from which the determination was made since the information from both flow and assay devices must be associated by a separate, self-governing process which is susceptible to corruption.

At flow rates less than 100 mL/min, an interference due to fine gas bubbles can be readily distinguishable from the turbidity value as a summary product of the interference value and the turbidity value. The fine gas bubbles can be observed as momentary perturbations in a baseline turbidity value. As a flow rate is increased for the liquid sample, a greater number of fine gas bubbles can more often be carried into the measurement chamber 108 of the turbidity measuring device 100 making the baseline determination and turbidity value less obvious. As the flow rate increases further, the frequency at which the interference value is superimposed upon the turbidity value continues to increase until a limit is reached wherein the baseline value becomes irreconcilable from the interference value. It can therefore be necessary to reduce the flow rate or alter the measurement step(s) and/or determination step(s) so as the resulting baseline value is no longer obscured by the fine bubble interference. For example, a flow rate at which the interference rate does not exceed the Nyquist limit of the interrogation or measurement rate.

As it can be readily observed that the rate of interference is related to a temperature, pressure, and flow rate of the liquid sample through the turbidity measuring device 100, a measure of one or more of a temperature, a pressure, and a flow rate of the liquid sample at a point of interrogation can be used to alter the measurement step(s) and/or determination step(s) to improve the detection limit of the liquid assay and to verify that the turbidity measuring device 100 is operating within recommended operational parameters of the device.

Per Henry's Law—at a given temperature, the solubility of a gas in a liquid is directly proportional to the partial pressure of the gas above the liquid:

$$s_g = p_g / k_H \quad (1)$$

Where
$s_g$=solubility of dissolved gas(mol/L)
$k_H$=proportionality constant depending on the nature of the gas and the solvent (mol/atm)
$p_g$=partial pressure of the gas (atm)

TABLE 1

| Gas | $S_g$ (atm/mol) |
|---|---|
| $O_2$ | 769.23 |
| $H_2$ | 1282.05 |
| $CO_2$ | 29.41 |
| $N_2$ | 1639.34 |
| He | 2702.70 |
| Ne | 2222.22 |
| Ar | 714.28 |
| CO | 1052.63 |

Table 1.—Solubility constants for aqueous gas and free gas at equilibrium at 298K (15.85 deg. C.). Since air is comprised mostly of argon, oxygen and nitrogen; (~0.01Ar, ~0.21 $O_2$, ~0.78 $N_2$), the amount of air in water at 298K at 1 atmosphere is equal to:

$$\frac{0.01 - 39.948}{714.28} + \frac{0.21 - 31.5588}{769.23} + \frac{0.78 - 28.0134}{1639.34} = 0.022624 \text{ g/L} \quad (2)$$

As the temperature of the water decreases, the capacity of the water for dissolved gases increases, (the solubility constants for the gases in Table 1 increase with temperature). Similarly, as the pressure above the water increases the capacity for dissolved gases in the solution increases. For oxygen a change from 0 to 30 degrees celcius changes the amount of dissolved oxygen from 14.6 to 7.6 ppm, (mg/L). The change in dissolved oxygen in water with a change in pressure is directly proportional to the pressure change.

In one embodiment, the turbidimeter 100 can detect a temperature of the liquid sample 190 within the measurement chamber 108 by the temperature sensor 150. Since the measurement chamber 108 can be vented to atmosphere, the change in amount of dissolved air in the liquid sample 190 due to atmospheric pressure change can be limited to a factor between 0.94 and 1.07 atm. Atmospheric pressure can be measured within the measurement module 102. For a given change in atmospheric pressure and/or temperature, an "outgas" potential may be calculated as a percent change in the amount of dissolved gases in the liquid sample 190. Similarly, for normal operational flow rates between 20 and 1000 ml/min, the turbidimeter 100 can be characterized for interference "carry" potential. "Carry" potential can be defined as the frequency at which fine gas bubble interferences are carried into the measurement chamber 108 as a function of flow rate. By considering the outgas potential and carry potential as part of the measurement step(s), the bubble rejection algorithm may be dynamically altered in the determination step(s) to reduce the standard error. As example, a harmonic mean algorithm as a bubble reject algorithm:

$$\frac{1}{H} = \frac{1}{n} \sum_{i=1}^{n} \frac{1}{x_i} \quad (3)$$

Where:
n=the number measurements within the turbidity value determination set
$x_i$=a measurement within the turbidity value determination set
H=harmonic mean When the carry potential and/or outgas potential is relatively high, the number of measurements considered for the determination of the turbidity value n can be increased providing a better statistical base for the removal of outlier measurements, thus reducing the standard error for a given turbidity determination. In a case when it is impractical to increase the number of measurements to be considered for the determination of a turbidity value, one or more of the sample parameters measured by the turbidimeter 100, for instance temperature, pressure, and/or flow rate, can be altered to reduce the interference rate to also reduce the standard error of the reported turbidity value.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:
1. A turbidity measuring device comprising:
a measurement module including:
an illumination module providing a beam of electromagnetic radiation; and
a detection module for measuring scattered electromagnetic radiation;
a fluidic module operatively coupled to the measurement module, the fluidic module including:
a first chamber adapted to receive a liquid;
a second chamber in fluid communication with the first chamber, the second chamber including a weir;

a third chamber in fluid communication with the second chamber, wherein liquid from the second chamber is adapted to spill into the third chamber via the weir; and a tube including at least one bend, the tube being positioned within the third chamber and being adapted to excommunicate the liquid from the turbidity measuring device;

wherein a turbidity of the liquid is determined based on an amount of electromagnetic radiation detected by the detection module and a flow rate of the liquid spilling from the second chamber to the third chamber.

2. The turbidity measuring device of claim 1, wherein the tube is an inverted substantially U-shaped tube.

3. The turbidity measuring device of claim 2, wherein the tube includes a first leg and a second leg being oriented substantially parallel to one another, the first leg being (i) longer than the second leg, and (ii) extending below a bottom of the third chamber.

4. The turbidity measuring device of claim 3, wherein the first leg and the second leg of the tube are each substantially perpendicular to a bottom of the third chamber.

5. The turbidity measuring device of claim 4, wherein an end of the first leg is located above the bottom of the third chamber.

6. The turbidity measuring device of claim 1, wherein an apex of the at least one bend is located below the weir.

7. The turbidity measuring device of claim 1, wherein a volume of liquid is drawn from the third chamber as a result of negative pressure created by a flow of liquid through the tube when liquid within the third chamber exceeds a height of the bend in the tube.

8. The turbidity measuring device of claim 1, wherein (i) the third chamber has a predetermined volume, and (ii) a flow rate of the excommunicating liquid from the second chamber is determined according to an elapsed time from one occurrence of a presence of liquid within the third chamber to a subsequent occurrence of the presence of liquid within the third chamber.

9. The turbidity measuring device of claim 1, wherein (i) the third chamber has a predetermined volume, and (ii) a flow rate of the excommunicating liquid from the second chamber is determined according to an elapsed time from one occurrence of an absence of liquid within the third chamber to a subsequent occurrence of the absence of liquid within the third chamber.

10. A method for determining a flow rate in a turbidity measuring device, the method comprising:

providing a turbidity measuring device, the turbidity measuring device including:
 a measurement module including:
  an illumination module providing a beam of electromagnetic radiation; and
  a detection module for measuring scattered electromagnetic radiation;
 a fluidic module operatively coupled to the measurement module, the fluidic module including:
  a first chamber adapted to receive a liquid;
  a second chamber in fluid communication with the first chamber, the second chamber being vented to atmosphere;
  a third chamber in fluid communication with the second chamber, wherein liquid from the second chamber is adapted to spill into the third chamber; and
  an inverted substantially U-shaped tube located in the third chamber;

introducing a liquid sample to the turbidity measuring device, the liquid sample flowing to the third chamber from the second chamber;

initiating a first fill and discharge cycle in the third chamber;

initiating a second fill and discharge cycle in the third chamber;

determining a flow rate of the liquid sample excommunicating from the second chamber to third chamber based on the first and second fill and discharge cycles; and determining a turbidity value based on an amount of electromagnetic radiation detected by the detection module and the flow rate of the liquid sample.

11. The method of claim 10, the first and second fill and discharge cycles each including:

filling the third chamber with the liquid sample until the inverted substantially U-shaped tube is completely submerged and filled with the liquid sample; and discharging the liquid sample from the turbidity measuring device until the inverted substantially U-shaped tube is emptied.

12. The method of claim 10, wherein the flow rate is determined as a volume of liquid discharged by the inverted substantially U-shaped tube divided by a time interval needed to discharge the volume liquid to a predetermined level within the third chamber.

13. A method for reducing a standard error for a given turbidity measurement, the method comprising:

providing a turbidity measuring device, the turbidity measuring device including:
 a measurement module including:
  an illumination module providing a beam of electromagnetic radiation;
  a detection module for measuring scattered electromagnetic radiation; and
  a pressure sensor adapted to measure a pressure of an atmosphere in the measurement module;
 a fluidic module operatively coupled to the measurement module, the fluidic module including:
  a first chamber adapted to receive a liquid;
  a second chamber in fluid communication with the first chamber, the second chamber being vented to atmosphere;
  a third chamber in fluid communication with the second chamber, wherein liquid from the second chamber is adapted to spill into the third chamber;
  a temperature sensor located in the second chamber; and
  an inverted substantially U-shaped tube located in the third chamber;

introducing a liquid sample to the turbidity measuring device;

determining a pressure in the measurement module;

determining a temperature of the liquid sample in the second chamber;

interrogating the liquid sample with the beam of electromagnetic radiation;

initiating a first fill and discharge cycle in the third chamber;

initiating a second fill and discharge cycle in the third chamber;

determining a flow rate of the liquid sample excommunicating from the second chamber to third chamber based on the first and second fill and discharge cycles; and determining a turbidity value based on (i) an amount of electromagnetic radiation detected by the detection module, (ii) the temperature of the liquid sample in the second chamber, (iii) the flow rate of the liquid sample, and (iv) the pressure in the measurement module.

14. A method for reducing a standard error for a given turbidity measurement, the method comprising:
providing a turbidity measuring device, the turbidity measuring device including:
a measurement module including:
an illumination module providing a beam of electromagnetic radiation;
a detection module for measuring scattered electromagnetic radiation; and
a pressure sensor adapted to measure a pressure of an atmosphere in the measurement module;
a fluidic module operatively coupled to the measurement module, the fluidic module including:
a first chamber adapted to receive a liquid;
a second chamber in fluid communication with the first chamber, the second chamber being vented to atmosphere;
a third chamber in fluid communication with the second chamber, wherein liquid from the second chamber is adapted to spill into the third chamber; and
an inverted substantially U-shaped tube located in the third chamber;
introducing a liquid sample to the turbidity measuring device;
determining a pressure in the measurement module;
interrogating the liquid sample with the beam of electromagnetic radiation;
initiating a first fill and discharge cycle in the third chamber;
initiating a second fill and discharge cycle in the third chamber;
determining a flow rate of the liquid sample excommunicating from the second chamber to third chamber based on the first and second fill and discharge cycles; and
determining a turbidity value based on (i) an amount of electromagnetic radiation detected by the detection module, (ii) the flow rate of the liquid sample, and (iii) the pressure in the measurement module.

15. A method for reducing a standard error for a given turbidity measurement, the method comprising:
providing a turbidity measuring device, the turbidity measuring device including:
a measurement module including:
an illumination module providing a beam of electromagnetic radiation; and
a detection module for measuring scattered electromagnetic radiation;
a fluidic module operatively coupled to the measurement module, the fluidic module including:
a first chamber adapted to receive a liquid;
a second chamber in fluid communication with the first chamber, the second chamber being vented to atmosphere;
a third chamber in fluid communication with the second chamber, wherein liquid from the second chamber is adapted to spill into the third chamber;
a temperature sensor located in the second chamber; and
an inverted substantially U-shaped tube located in the third chamber;
introducing a liquid sample to the turbidity measuring device;
determining a temperature of the liquid sample in the second chamber;
interrogating the liquid sample with the beam of electromagnetic radiation;
initiating a first fill and discharge cycle in the third chamber;
initiating a second fill and discharge cycle in the third chamber;
determining a flow rate of the liquid sample excommunicating from the second chamber to third chamber based on the first and second fill and discharge cycles; and
determining a turbidity value based on (i) an amount of electromagnetic radiation detected by the detection module, (ii) the temperature of the liquid sample in the second chamber, and (iii) the flow rate of the liquid sample.

16. A turbidity measuring device comprising:
a measurement module including:
an illumination module providing a beam of electromagnetic radiation;
a detection module for measuring scattered electromagnetic radiation; and
a pressure sensor adapted to measure a pressure of an atmosphere in the measurement module;
a fluidic module operatively coupled to the measurement module, the fluidic module including:
a first chamber adapted to receive a liquid;
a second chamber in fluid communication with the first chamber, the second chamber being vented to atmosphere;
a third chamber in fluid communication with the second chamber, wherein liquid from the second chamber is adapted to spill into the third chamber; and
a tube including at least one bend, the tube being positioned within the third chamber and being adapted to excommunicate the liquid from the turbidity measuring device;
wherein a turbidity of the liquid is determined based on (i) an amount of electromagnetic radiation detected by the detection module, (ii) a flow rate of the liquid spilling from the second chamber to the third chamber, and (iii) a pressure in the measurement module located above the liquid within the second chamber.

17. A turbidity measuring device comprising:
a measurement module including:
an illumination module providing a beam of electromagnetic radiation; and
a detection module for measuring scattered electromagnetic radiation;
a fluidic module operatively coupled to the measurement module, the fluidic module including:
a first chamber adapted to receive a liquid;
a second chamber in fluid communication with the first chamber, the second chamber being vented to atmosphere;
a third chamber in fluid communication with the second chamber, wherein liquid from the second chamber is adapted to spill into the third chamber;
a temperature sensor adapted to measure a temperature of the liquid in the second chamber; and
a tube including at least one bend, the tube being positioned within the third chamber and being adapted to excommunicate the liquid from the turbidity measuring device;

wherein a turbidity of the liquid is determined based on (i) an amount of electromagnetic radiation detected by the detection module, (ii) a temperature of the liquid within the second chamber, and (iii) a flow rate of the liquid spilling from the second chamber to the third chamber.

18. A turbidity measuring device comprising:
a measurement module including:
- an illumination module providing a beam of electromagnetic radiation;
- a detection module for measuring scattered electromagnetic radiation; and
- a pressure sensor adapted to measure a pressure of an atmosphere in the measurement module;

a fluidic module operatively coupled to the measurement module, the fluidic module including:
- a first chamber adapted to receive a liquid;
- a second chamber in fluid communication with the first chamber, the second chamber being vented to atmosphere;
- a third chamber in fluid communication with the second chamber, wherein liquid from the second chamber is adapted to spill into the third chamber;
- a temperature sensor adapted to measure a temperature of the liquid in the second chamber; and
- a tube including at least one bend, the tube being positioned within the third chamber and being adapted to excommunicate the liquid from the turbidity measuring device;

wherein a turbidity of the liquid is determined based on (i) an amount of electromagnetic radiation detected by the detection module, (ii) a flow rate of the liquid spilling from the second chamber to the third chamber, (iii) a temperature of the liquid within the second chamber, and (iv) a pressure in the measurement module located above the liquid within the second chamber.

* * * * *